United States Patent
Huang et al.

(10) Patent No.: US 12,252,459 B2
(45) Date of Patent: Mar. 18, 2025

(54) HYDRAZONE AMIDE DERIVATIVES AND USE THEREOF IN PREPARATION OF ANTI-OSTEOPOROSIS DRUGS

(71) Applicant: SHENZHEN CELL INSPIRE PHARMACEUTICAL DEVELOPMENT CO., LTD., Guangdong (CN)

(72) Inventors: Dane Huang, Guangdong (CN); Chao Zhao, Guangdong (CN); Qiong Gu, Guangdong (CN); Jun Xu, Guangdong (CN)

(73) Assignee: SHENZHEN CELL INSPIRE PHARMACEUTICAL DEVELOPMENT CO., LTD., Guangdong (CN)

( * ) Notice: Subject to any disclaimer, the term of this patent is extended or adjusted under 35 U.S.C. 154(b) by 641 days.

(21) Appl. No.: 17/562,040

(22) Filed: Dec. 27, 2021

(65) Prior Publication Data
US 2022/0153688 A1    May 19, 2022

Related U.S. Application Data

(63) Continuation of application No. PCT/CN2020/083067, filed on Apr. 2, 2020.

(30) Foreign Application Priority Data

Jun. 28, 2019    (CN) .......................... 201910578809.5

(51) Int. Cl.
| | | |
|---|---|---|
| *A61P 19/10* | (2006.01) | |
| *A61K 31/15* | (2006.01) | |
| *A61K 31/426* | (2006.01) | |
| *A61K 31/428* | (2006.01) | |
| *A61K 31/4465* | (2006.01) | |
| *A61K 31/472* | (2006.01) | |
| *A61K 31/5375* | (2006.01) | |
| *A61P 19/08* | (2006.01) | |
| *C07C 251/76* | (2006.01) | |
| *C07D 211/58* | (2006.01) | |
| *C07D 213/75* | (2006.01) | |
| *C07D 213/80* | (2006.01) | |
| *C07D 213/84* | (2006.01) | |
| *C07D 217/06* | (2006.01) | |
| *C07D 277/56* | (2006.01) | |
| *C07D 277/82* | (2006.01) | |
| *C07D 295/185* | (2006.01) | |
| *C07D 417/12* | (2006.01) | |

(52) U.S. Cl.
CPC .......... *C07C 251/76* (2013.01); *A61K 31/15* (2013.01); *A61K 31/426* (2013.01); *A61K 31/428* (2013.01); *A61K 31/4465* (2013.01); *A61K 31/472* (2013.01); *A61K 31/5375* (2013.01); *A61P 19/08* (2018.01); *A61P 19/10* (2018.01); *C07D 211/58* (2013.01); *C07D 213/75* (2013.01); *C07D 213/80* (2013.01); *C07D 213/84* (2013.01); *C07D 217/06* (2013.01); *C07D 277/56* (2013.01); *C07D 277/82* (2013.01); *C07D 295/185* (2013.01); *C07D 417/12* (2013.01)

(58) Field of Classification Search
CPC .......... A61P 19/08; A61P 19/10; A61K 31/42; A61K 31/428; A61K 31/4465; A61K 31/472; A61K 31/5375; A61K 31/15
See application file for complete search history.

(56) References Cited

U.S. PATENT DOCUMENTS

2016/0280925 A1    9/2016    Kawamura et al.

FOREIGN PATENT DOCUMENTS

| CN | 1084512 A | 3/1994 |
|---|---|---|
| CN | 2015067576 A | 4/2015 |
| CN | 105796545 A | 7/2016 |
| CN | 107372496 A | 11/2017 |
| CN | 110229118 A | 9/2019 |
| CN | 110330465 A | 10/2019 |
| EP | 1790697 A1 | 5/2007 |
| EP | 2316885 A1 | 5/2011 |
| JP | 2003505503 A | 2/2003 |
| JP | 2013182058 A | 9/2013 |
| JP | 2016148729 A | 8/2016 |
| JP | 2022540062 A | 9/2022 |
| WO | 2009137471 A2 | 11/2009 |

OTHER PUBLICATIONS

Notice of Reasons for Refusal in Japanese Patent Application No. 2021-577960, dated Aug. 29, 2023.
(Continued)

*Primary Examiner* — Laura L Stockton

(57) ABSTRACT

Provided are a new class of hydrazone amide derivatives and the use thereof in the preparation of anti-osteoporosis drugs, wherein the structural formula of the hydrazone amide derivative is as shown in formula (I), and same are a new class of compounds with an anti-osteoporosis effect.

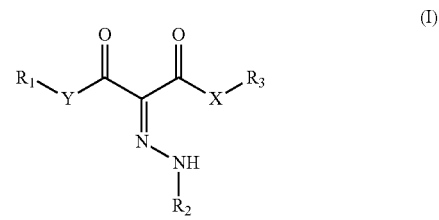

2 Claims, 10 Drawing Sheets

(56) References Cited

OTHER PUBLICATIONS

The extended European search report in European Patent application No. 20831187.8, dated Aug. 12, 2022.
Atash V. Gurbanov et al., "The Henry reaction catalyzed by Ni II and Cu II complexes bearing arylhydrazones of acetoacetanilide", Journal of Organometallic Chemistry, vol. 869, 2018, pp. 48-53, XP055948037, ISSN: 0022-328X, DOI: 10.1016/j.jorganchem.2018.05.025.
Poskocil J. et al., "Aromatic Diazo and Azo Compounds XX. Oxidation of Dyes Produced From Acetacetic Acid Anilide", Collection of Czechoslovak Chemical Communications, vol. 21, No. 4. 1956, pp. 920-925, XP055947906, ISSN: 0010-0765, DOI: 10.1135/cccc19560920.
Database Registry [Online], Nov. 16, 1984 (Nov. 16, 1984), Anonymous: "Benzoic acid, 4-[2-[1-[[(2,4-dimethylphenyl)amino]carbonyl]-2-oxopropylidene]hydrazinyl]— (CA Index Name)", XP055885855, retrieved from STN, Database accession No. 63239-94-1.
Rajeev Jain et al., "Synthesis of some New I-Carbamoyl-3-aminophenyl- and I-Carbamoyl-3-amino-(2-chlorophenyl)-5-methyl-4-arylazopyrazoles as Possible Potential Antidiabetics", J. Indian Chem. Soc., vol. 66, Jul. 1989, pp. 486-489, XP009533298.
Rajeev Jain et al., "Synthesis of some New Arylazopyrazoles and Arylazopyrimidines", J. Indian Chem. Soc., vol. 67, 1990, pp. 516-518, XP009533296.
Zhen Ma et al., "Effective cyanosilylation of aldehydes with copper(II)-based ploymeric catalysts", Journal of Molecular Catalysis A: Chemical, vol. 428, 2017, pp. 17-23, XP055773260.
Murat Çağlar Hamzaçebi et al., "Synthesis and structure elucidation of hydrazones derived from N-(2,4-dimethylphenyl)-3-oxobutanamide", Arkivoc, vol. xii, 2008, pp. 188-194, XP055773381.
Communication pursuant to Article 94(3) EPC in European Patent Application No. 20 831 187.8, dated Apr. 19, 2023.
Notice of Reasons for Refusal in Japanese Patent Application No. 2021-577960, dated Jan. 31, 2023.
Antonius Kettrup et al., "The Fragmentation of Azo and Hydrazone Tautomeres of 2,3-Dioxobutyranilide-2-phenylhydrazones in the Gaseous State in Dependence of Substituents", Zeitschrift fur Naturforschung B, 1977, vol. 32, No. 8, pp. 863-868, DOI: 10.1515/znb-1977-0806.
Sujit Suresh Kamble et al., "Room temperature diazotization and coupling reaction using a DES-ethanol system: a green approach towards the synthesis of monoazo pigments", Chem. Commun., vol. 55, No. 42, Apr. 25, 2019, ISSN: 1359-7345, pp. 5970-5973, in particular figure 4, DOI: 10.1039/c9cc01114e.
Zhen Ma et al., "Effective cyanosilylation of aldehydes with copper(II)-based polymeric catalysts", Journal of Molecular Catalysis A: Chemical, vol. 428, Nov. 28, 2016, ISSN: 2468-8231, pp. 17-23, particularly Scheme 2.
Qian Zhang et al., "Formal [4+1] annulation of α-arylhydrazonoketones and dimethylsulfoxonium methylide: one-pot synthesis of substituted pyrazoles and dihydropyrazoles", The Journal of Organic Chemistry, vol. 81, No. 14, Jun. 21, 2016, ISSN: 0022-3263, pp. 6036-6041, in particular figure 2.
Zheng Li et al., "The influence of fluorination on the structure and properties of azo pigments", Dyes and Pigments, vol. 128, Feb. 3, 2016, ISSN: 0143-7208, pp. 246-255, in particular figure 1.
Pratibha Sharma et al., "Studies on synthesis and evaluation of quantitative structure-activity relationship of 5-[(3'-chloro-4',4'-disubstituted-2-oxoazetidinyl)(N-nitro)amino]-6-hydroxy-3-alkyl/aryl[1,3]azaphospholo[1,5-a]pyridin-1-yl-phosphorus dichlorides", Bioorganic & Medicinal Chemistry Letters, vol. 15, No. 4, Jan. 20, 2005, ISSN: 0960-894X, pp. 937-943, in particular Table 1, Scheme 1.
A. S. Shawali et al., "Cyanoacetarylamides-I Preparation and reactions of their arylazo derivatives with diazonium ion and Grignard reagents", Tetrahedron, vol. 27, No. 10, Dec. 31, 1971, ISSN: 0040-4020, pp. 4305-4316, in particular Scheme 4.
C. W. Schellhammer et al., "Über Alkylierungen Von Benzotriazol-Derivaten", Tetrahedron, vol. 26, No. 2, Dec. 31, 1970, ISSN: 0040-4020, pp. 497-510, in particular p. 499.
M. A. Aboutabl et al., "Polarographic behaviour of α-and γ-substituted acetoacetanilide derivatives in alcoholic aqueous media", Monatshefte für Chemie, vol. 123, No. 3, Mar. 31, 1992, ISSN: 0026-9247, pp. 217-223, in particular p. 218.
Rajeev Jain et al., "Synthesis of some new arylazopyrazoles and arylazopyrimidines", Journal of the Indian Chemical Society, vol. 67, No. 6, Jun. 30, 1990, ISSN: 0019-4522, pp. 516-517.
Antonin Lycka et al., "15N, 13C and 1H NMR spectra of the 2:1 cobalt(III) complexes of some azo dyes", Magnetic Resonance in Chemistry, vol. 28, May 31, 1990, ISSN: 0749-1581, pp. 408-413, particularly Scheme 2.
Antonius Kettrup et al., "Spektroskopische untersuchungen an substituierten 2,3-dioxobutyranilid-2-phenylhydrazonen", Monatshefte für Chemie, vol. 107, No. 6, Dec. 31, 1976, ISSN: 0026-9247, pp. 1391-1411, in particular Table 1.
M.A. Zayed et al., "The use of thermal and spectrometric analyses for the structure investigation of arylhydrazoneacetoacetylaminopyridines and their copper chelates", Thermochimica Acta, vol. 146, Dec. 31, 1989, ISSN: 0040-6031, pp. 1-13, in particular pp. 1-2.
Robert M. Christie et al., "Colour and constitution relationships in organic pigments. Part 1.—Monoazoacetoacetanilides", Dyes and Pigments, vol. 9, No. 1, Dec. 31, 1988, ISSN: 0143-7208, pp. 37-56, in particular p. 39, compounds, table 8.
Greig Chisholm et al., "Comparison of the structural motifs of acetoacetanilides and related azo pigments", Acta Crystallographica Section B: Structural Science, vol. B56, No. 6, Dec. 31, 2000, ISSN: 0108-7681, pp. 1046-1053, in particular Table 1, section 2.1.
Poul Erik Hansen et al., "Long-range intrinsic and equilibrium deuterium isotope effects on19F chemical shifts", Acta Chemica Scandinavica, vol. 51, No. 8, Aug. 31, 1997, ISSN: 0904-213X, pp. 881-888, particularly Scheme 1.
A. A. Fadda et al., "Synthesis of azodisperse dyes with pyridine ring for dyeing polyester fibres", Indian Journal of Textile Research, vol. 11, No. 1, Mar. 31, 1986, ISSN: 0377-8436, pp. 44-47, in particular Table 1.
Murat Çaglar Hamzaçebi et al., "Synthesis and structure elucidation of hydrazones derived from N-(2,4-dimethylphenyl)-3-oxobutanamide", Arkivoc, vol. 2008, No. 12, May 21, 2008, ISSN: 1551-7012, pp. 188-194, particularly Scheme 2.
K. M. Dyumaev et al., "Synthesis and structure of 2-(2-phenylhydrazono)acetoacetanilide and its derivatives", Zhurnal Organicheskoi Khimii, vol. 14, No. 3, Dec. 31, 1978, ISSN: 0514-7492, pp. 562-569, in particular pp. 564-566.
Antonius Kettrup et al., "The fragmentation of azo and hydrazone tautomers of 2,3-dioxobutyranilide-2-phenylhydrazones in the gaseous state in dependence of substituents", Z. Naturforsch, vol. 32b, No. 8, Aug. 31, 1977, ISSN: 0340-5087, pp. 863-868, in particular Tab.I.
Rajeev Jain et al., "Synthesis of some new isonicotinoylazopyrazoles", Journal of the Indian Chemical Society, vol. 66, No. 5, May 31, 1989, ISSN: 0019-4522, pp. 350-352, in particular p. 350, Table 1.
Rajeev Jain et al., "Synthesis of some new 1-carbamoyl-3-aminophenyl- and 1-carbamoyl-3-amino-(2-chlo-rophenyl)-5-methyl-4-arylazopyrazoles as possible potential antidiabetics", Journal of the Indian Chemical Society, vol. 66, No. 7, Jul. 31, 1989, ISSN: 0019-4522, pp. 486-489, in particular Table 1.
Dietrich Moderhack et al., "1,2,5,6-Tetrazocines from Nitrile Imines and tert-Butyl Isocyanide", J. Prakt. Chem., vol. 342, No. 7, Aug. 17, 2000, ISSN: 1436-9966, pp. 707-710, particularly Scheme 1.
R N Goyal et al., "Electro-chemical investigations of some acetoacetarylides", Indian Journal of Chemistry, (vol. 23A), No. 11, Nov. 30, 1984, ISSN: 0376-4710, pp. 900-903, in particular Table 1.
M. I. Ali et al., "Reactions with acetoacetylaminopyridines", Egyptian Journal of Chemistry, vol. 30, No. 5, 1987, ISSN: 0367-0422, pp. 357-368, in particular p. 361.
CAS registry on STN CAS-RN: 2324187-36-0 (Jun. 4, 2019); 1455518-21-4 (Oct. 4, 2013); 1274906-03-4 (Apr. 5, 2011); 1235682-03-7 (Aug. 10, 2010); 358718-99-7 (Sep. 26, 2001); 331968-10-6

(56) References Cited

OTHER PUBLICATIONS (Apr. 20, 2001); 331416-65-0 (Apr. 16, 2001); 314763-74-1 (Jan. 18, 2001); 174011-08-6 (Mar. 8, 1996); 174011-05-3 (Mar. 8, 1996); 94959-92-9 (Feb. 24, 1985); 94674-38-1 (Feb. 9, 1985); 94207-41-7 (Jan. 12, 1985); 94207-07-5 (Jan. 12, 1985); 94206-41-4 (Jan. 12, 1985).
CAS registry on STN CAS-RN: 93021-19-3 (Dec. 18, 1984); 93021-18-2 ((Dec. 18, 1984); 93021-17-1 ((Dec. 18, 1984); 92873-78-4 ((Dec. 17, 1984); 90422-20-1 (Nov. 16, 1984); 63239-95-2 (Nov. 16, 1984); 63239-94-1 (Nov. 16, 1984); 63239-82-7 (Nov. 16, 1984); 63239-81-6 (Nov. 16, 1984); 50599-23-0 (Nov. 16, 1984); 2324187-34-8 (Jun. 4, 2019).
Atash V. Gurbanov et al., "Copper(II) complexes with carboxylic- or sulfonic-functionalized arylhydrazones of acetoacetanilide and their application in cyanosilylation of aldehydes", Journal of Organometallic Chemistry, 834, 2017, pp. 22-27.
CAS registry on STN CAS-RN: 331968-10-6, Apr. 20, 2001.

HYDRAZONE AMIDE DERIVATIVES AND USE THEREOF IN PREPARATION OF ANTI-OSTEOPOROSIS DRUGS

CROSS-REFERENCE TO RELATED APPLICATION

The present application is a continuation of International Patent Application No. PCT/CN2020/083067, filed on Apr. 2, 2020, which claims priority to Chinese patent application NO. 201910578809.5, filed on Jun. 28, 2019, the entire contents of which are incorporated herein by their references.

TECHNICAL FIELD

The present disclosure relates to the field of biomedicine, and particularly, the present disclosure relates to hydrazone amide derivatives and use thereof as osteoclast differentiation inhibitors in preparation of anti-osteoporosis drugs.

BACKGROUND

Osteoporosis (OP) is a systemic bone disease characterized by the decreased bone mass, and the increased bone fragility and fracture risk caused by destruction of the fine structure of bone tissues. The main clinical manifestations and signs are pains, followed by shortened body length, hunchback, fractures, and respiratory disorders. Epidemiological investigation shows that about 50% of women and 20% of men among people over age 50 are at risk of fractures (Rachner, Khosla et al. 2011).

A proportional imbalance between osteoclasts and osteoblasts is the pathological basis of the onset of osteoporosis (Rachner, Khosla et al. 2011). Both the relative increase in osteoclast differentiation or the relative decrease in osteoblast differentiation will cause a loss of bone mass, leading to osteoporosis. The main clinical therapeutic options for osteoporosis are to reduce bone resorption and promote bone formation. Bone resorption inhibitors mainly include: estrogen receptor modulators, such as tamoxifen, toremifene, droloxifene, raloxifene, arzoxifene, bazedoxifene, ipriflavone, etc.; diphosphates such as phosphinate glycolate, clodronate, pamidronate, halogen phosphates, alendronic acid, risedronate sodium, zoledronic acid, ibandronate sodium, etc.; and calcitonin etc. The drugs for promoting bone formation mainly include Wnt signal regulators (AMG785, BHQ880), parathyroid hormone (PTH), calcium-sensitive receptor antagonists such as ATF936, and statins. There are also preparations that both inhibit bone resorption and promote bone formation, such as alfacalcidol, calcitriol, RO-26-9228, ED-71, and the like. Although the above-mentioned drugs can prevent the decrease of bone density to a certain extent, they cannot significantly reduce the risk of atypical fractures and are accompanied by different degrees of side effects, failing to meet the requirements of anti-osteoporosis treatment (Siris, Selby et al. 2009). Therefore, it is urgent to develop a new specific anti-osteoporosis medicament to solve the problem that existing clinical drugs cannot meet the treatment needs.

Osteoclast is a terminally differentiated cell derived from the bone marrow macrophage cell line, and is the only cell that is known to have bone resorption. Receptor activator of nuclear factor kappa B ligand (RANKL) is a transmembrane soluble protein necessary for osteoclasts to maintain their structure, function and survival. RANKL binds to its receptor to activate downstream NF-κB and Akt, mitogen-activated protein kinase (MAPK) and to activate T cell nuclear receptor (NFAT), calcium ion channels, and calcium/calmodulin-dependent kinase signaling pathway, thereby allowing the undifferentiated bone marrow macrophages to differentiate into osteoclasts, which in turn causes osteoporosis (Boyle, Simonet et al. 2003). A large number of studies have confirmed that interfering with the RANKL signaling pathway can inhibit osteoclast differentiation, so as to produce anti-osteoporosis pharmacological effects (Kim and Kim 2016). In recent years, it has become a scientific hot spot to develop new anti-osteoporosis drugs through interfering with the RANKL signaling pathway. It is expected to solve the problems of existing osteoporosis treatment drugs by searching for drugs having an inhibitory activity on the osteoclasts induced by RANKL.

SUMMARY

In view of the deficiencies in the related art, based on the new target, the RANKL signaling pathway, the present disclosure provides a new anti-osteoporosis medicament to overcome the problem that the existing osteoporosis treatment drugs cannot reduce the risk of atypical fractures. Thus, the present disclosure provides a new class of hydrazone amide derivatives and use thereof in preparation of anti-osteoporosis drugs.

In a first aspect of the present disclosure, the present disclosure provides a compound represented by formula (I), or a stereoisomer, geometric isomer, tautomer, nitrogen oxide, hydrate, solvate, metabolite, pharmaceutically acceptable salt or prodrug of the compound represented by formula (I),

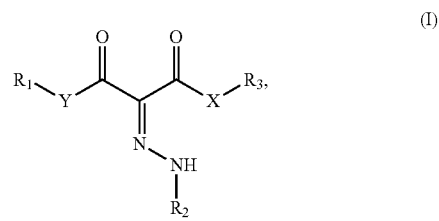

wherein X and Y are each independently selected from $C_1$-$C_6$ alkyl, hydroxyl, sulfydryl, amino, nitro, or cyano, wherein the $C_1$-$C_6$ alkyl, the hydroxyl, the sulfydryl, and the amino are independently substituted with $R_1$ or $R_3$, wherein $R_1$ and $R_3$ are each independently selected from hydrogen, cyano, nitro, alkoxy, alkylamino, hydroxyl, amino, fluorine, chlorine, bromine, linear alkyl, cycloalkyl, alkenyl, a five- to ten-membered heterocyclic ring, a five- to ten-membered heteroaromatic ring, or a benzene ring; or $R_1$ together with Y or $R_3$ together with X forms a five- to ten-membered heterocyclic ring or a five- to ten-membered heteroaromatic ring, wherein the linear alkyl, the cycloalkyl, the alkenyl, the five- to ten-membered heterocyclic ring, the five- to ten-membered heteroaromatic ring, and the benzene ring are optionally and independently substituted with R';

$R_2$ is selected from cyano, nitro, alkoxy, alkylamino, cycloalkyl, linear alkyl, alkenyl, a five- to six-membered ring, a five- to six-membered heteroaromatic ring, or a benzene ring, wherein the linear alkyl, the cycloalkyl, the alkenyl, the five- to six-membered ring, the five- to six-membered heteroaromatic ring, and the benzene ring are optionally and independently substituted by R'; and R' is hydrogen, halogen, $C_1$-$C_5$ alkoxy, $C_1$-$C_5$ alkyl, an ester group, nitro, hydroxyl, sulfydryl, carboxyl, amino, cyano, alkynyl, trifluoromethyl, or trifluoromethoxy.

According to an embodiment of the present disclosure, X is an oxygen atom or an amine group; and Y is $C_1$-$C_4$ alkylene, an oxygen atom, or an amine group.

According to an embodiment of the present disclosure, $R_1$ is hydrogen or linear $C_1$-$C_3$ alkyl.

According to an embodiment of the present disclosure, $R_2$ is phenyl, 2-carboxyphenyl, 3-carboxyphenyl, 4-carboxyphenyl, 2-hydroxyphenyl, 2-methoxyphenyl, 2-methylhydroxyphenyl, 2-aminophenyl, 2-amidophenyl, 2-carbomethoxyphenyl, 2-nitrophenyl, 2-cyanophenyl, 2,3-dicarboxyphenyl, 2,4-dicarboxyphenyl, 2,6-dicarboxyphenyl, 2,5-dicarboxyphenyl, 2-carboxy-3-methylphenyl, 2-carboxy-4-methylphenyl, 2-carboxy-5-methylphenyl, 2-carboxy-6-methylphenyl, 2-carboxy-3-fluorophenyl, 2-carboxy-4-fluorophenyl, 2-carboxy-5-fluorophenyl, 2-carboxy-6-fluorophenyl, 2-carboxy-3-hydroxyphenyl, 2-carboxy-4-hydroxyphenyl, 2-carboxy-5-hydroxyphenyl, 2-carboxy-6-hydroxyphenyl, 2-carboxy-3-aminophenyl, 2-carboxy-4-aminophenyl, 2-carboxy-5-aminophenyl, 2-carboxy-6-aminophenyl, 2-carboxy-6-trifluoromethylphenyl, 2-carboxy-3-trifluoromethylphenyl, 2-carboxy-4-trifluoromethylphenyl, 2-carboxy-5-trifluoromethylphenyl, 2-carboxy-6-methoxyphenyl, 2-carboxy-3-m ethoxyphenyl, 2-carboxy-4-m ethoxyphenyl, 2-carboxy-5-methoxyphenyl, 2-carboxy-3-chlorophenyl, 2-carboxy-4-chlorophenyl, 2-carboxy-5-chlorophenyl, 2-carboxy-6-chlorophenyl, 2-carboxy-3-cyanophenyl, 2-carboxy-4-cyanophenyl, 2-carboxy-5-cyanophenyl, 2-carboxy-6-cyanophenyl, 2-carboxy-3-nitrophenyl, 2-carboxy-4-nitrophenyl, 2-carboxy-5-nitrophenyl, or 2-carboxy-6-nitrophenyl.

According to an embodiment of the present disclosure, $R_3$ is thiazolyl, 4-methylthiazolyl, 4-methyl-5-ethoxycarbonylthiazolyl, 4-methyl-5-carbomethoxythiazolyl, 4-methyl-5-carboxythiazolyl, 4-methyl-5-formylmorpholinylthiazolyl, 4-phenylthiazolyl, thienyl, imidazolyl, pyridinyl, 6-carbomethoxypyridinyl, morpholinyl, 2-methylpyridinyl, 3-methylpyridinyl, 4-methylpyridinyl, 5-methylpyridinyl, 6-methylpyridinyl, 2-cyanopyridinyl, 3-cyanopyridinyl, 4-cyanopyridinyl, 5-cyanopyridinyl, 6-cyanopyridinyl, 2-nitropyridinyl, 3-nitropyridinyl, 4-nitropyridinyl, 5-nitropyridinyl, 6-nitropyridinyl, 2-hydroxypyridinyl, 3-hydroxypyridinyl, 4-hydroxypyridinyl, 5-hydroxypyridinyl, 6-hydroxypyridinyl, 2-methoxypyridinyl, 3-methoxypyridinyl, 4-methoxypyridinyl, 5-methoxypyridinyl, 6-methoxypyridinyl, 4-hydroisoquinolyl, phenyl, or benzothiazolyl.

According to an embodiment of the present disclosure, $R_1$ is hydrogen or $C_1$-$C_4$ alkyl; $R_2$ is a benzene ring, a pyridine ring, a pyrimidine ring, or a pyrazine ring; and $R_3$ is a five- to six-membered heterocyclic ring containing N or O, a five-membered heteroaromatic ring containing N, O or S, a six-membered heteroaromatic ring containing one or two nitrogen atoms, a benzene ring, or

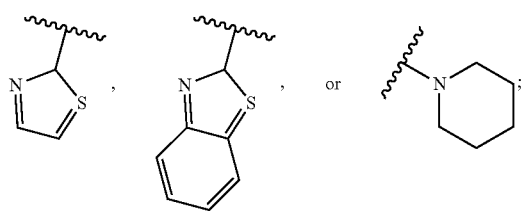

or $R_3$ together with X forms a five- to ten-membered heterocyclic ring containing an N atom or an O atom.

According to an embodiment of the present disclosure, $R_1$ is hydrogen; $R_2$ is a benzene ring; $R_3$ is a pyridine ring, a pyrimidine ring, a pyrazine ring,

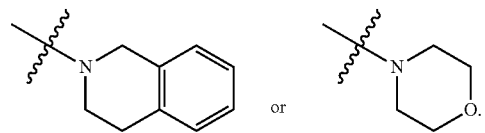 [SMILES: *N1CCc2ccccc2C1 ; "or" ; *N1CCOCC1]

or $R_3$ together with X forms

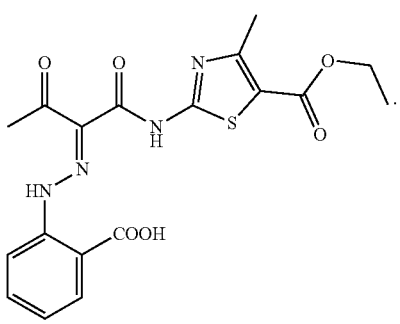

According to an embodiment of the present disclosure, the compound does not comprise a compound represented by formula (1):

1

According to an embodiment of the present disclosure, it is a compound having one of the following structures, or a stereoisomer, geometric isomer, tautomer, nitrogen oxide, hydrate, solvate, metabolite, pharmaceutically acceptable salt or prodrug of the compound having one of the following structures:

1
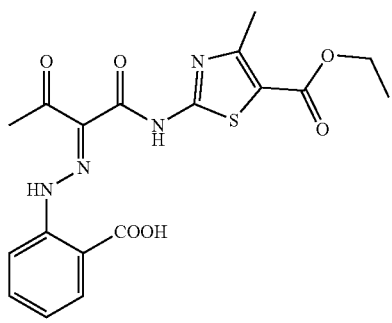
2
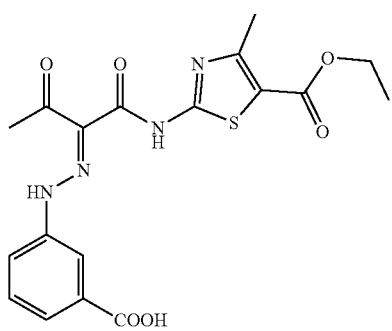
3
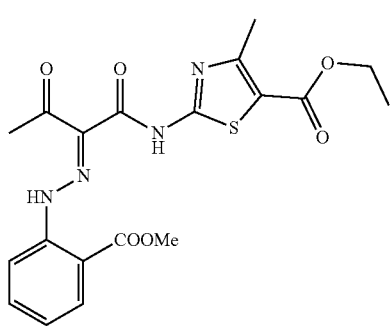
4
5
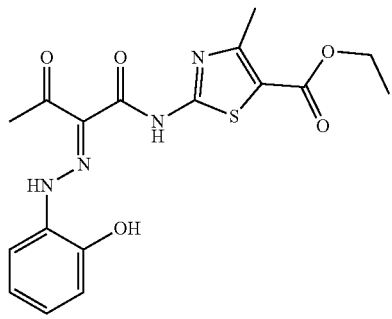
6
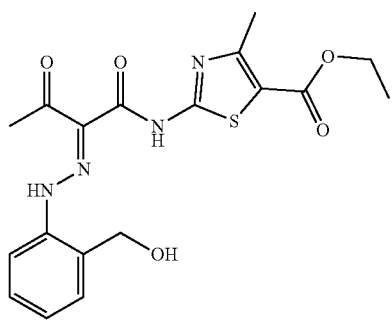
7
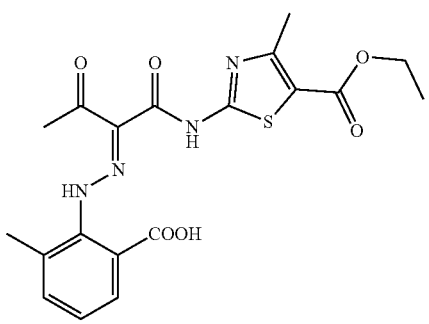
8
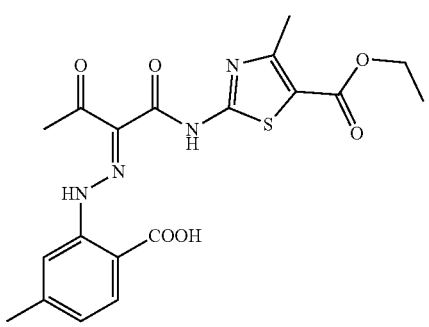
9

10
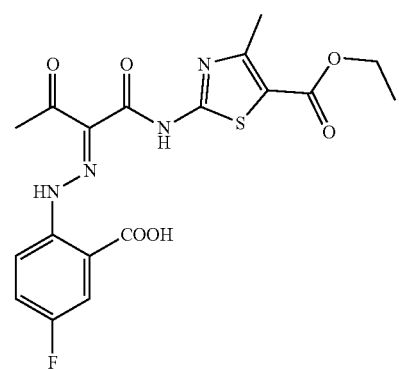
11
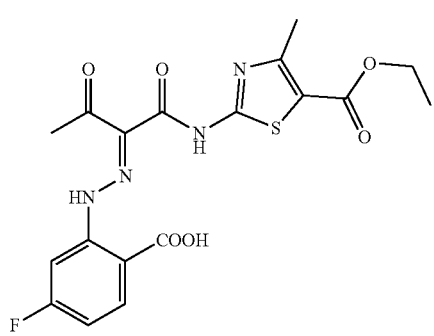
12
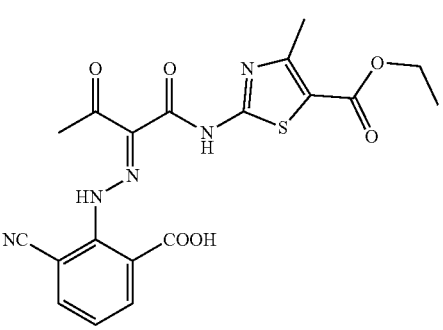
13
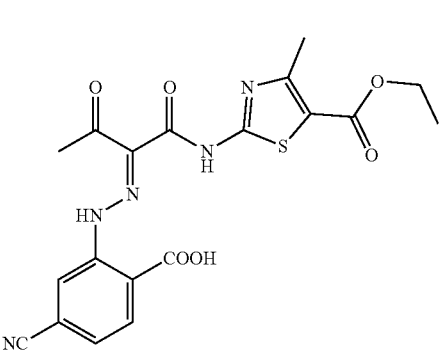
14
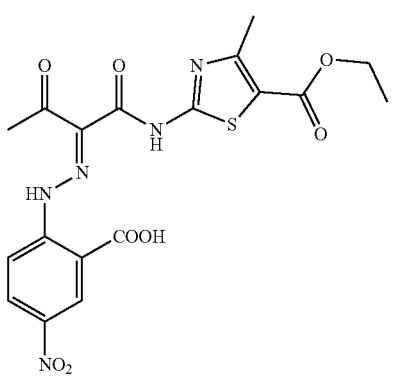
15
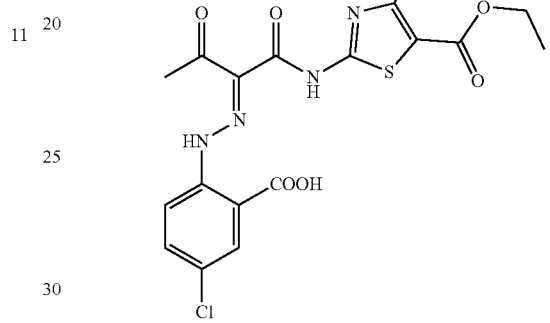
16
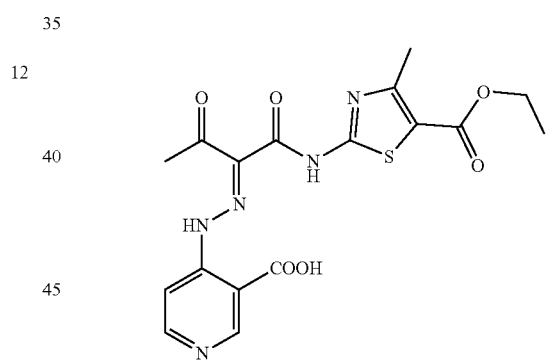
17
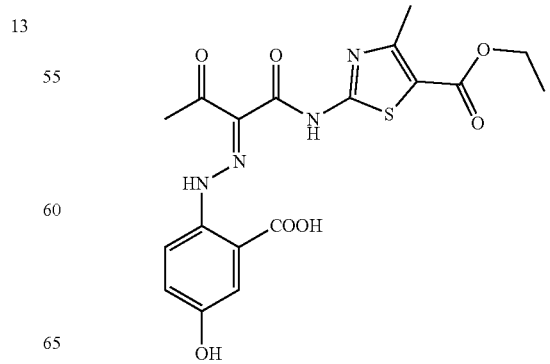

18
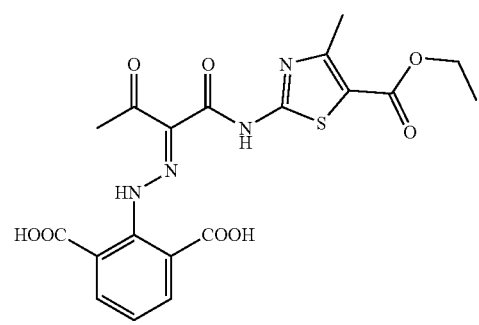
19
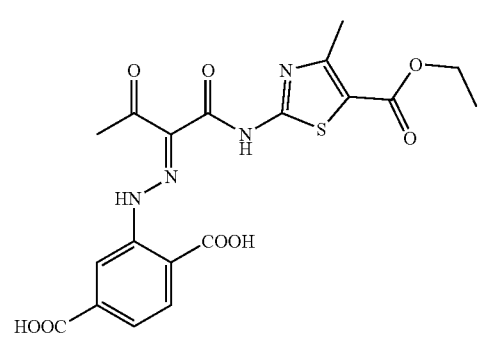
20
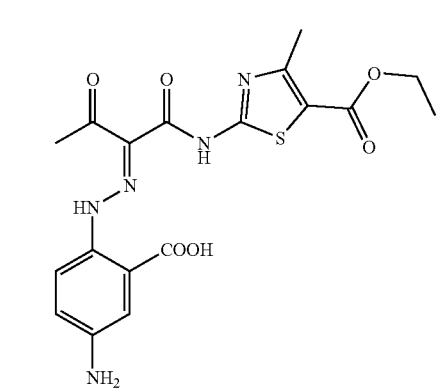
21
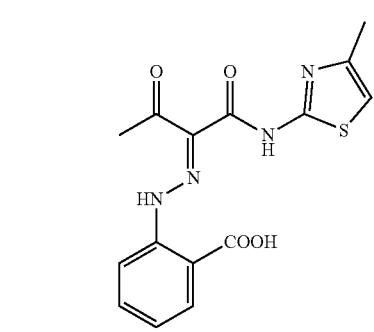
22
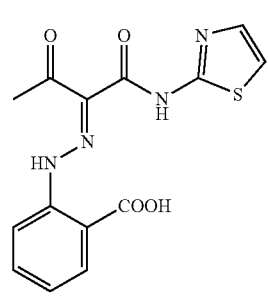
23
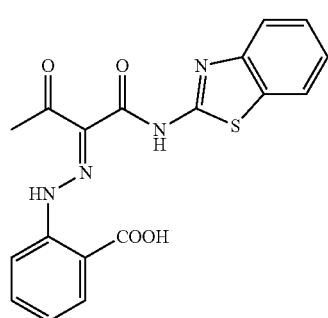
24
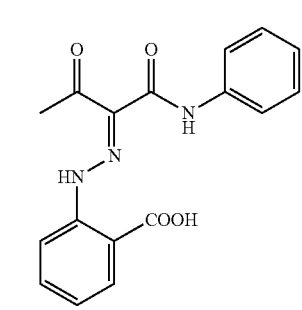
25
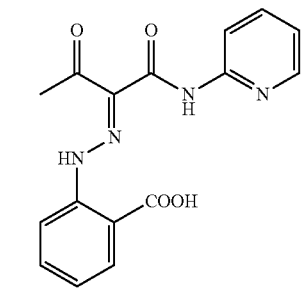
26
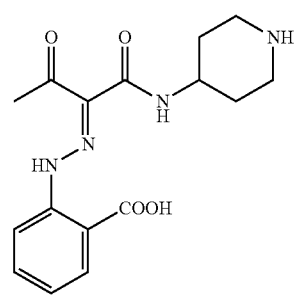
27
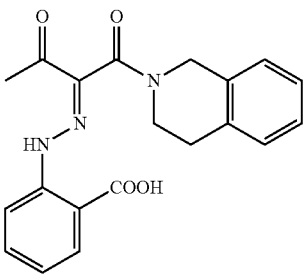

-continued

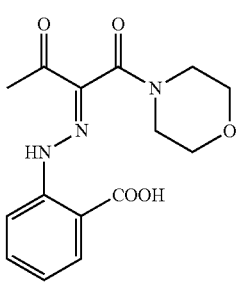

28

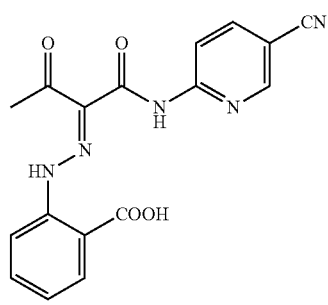

29

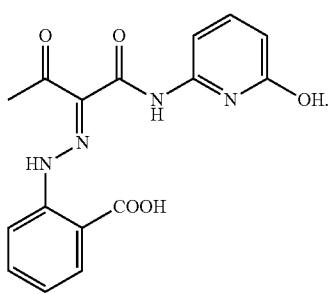

30

As a preferred embodiment, among the above structures, compounds 3, 10, 12, 18, and 25 have significant effects in terms of both inhibitory activity and safety.

In a second aspect of the present disclosure, the present disclosure provides a pharmaceutical composition. According to an embodiment of the present disclosure, the pharmaceutical composition includes the compound as described above.

According to an embodiment of the present disclosure, the pharmaceutical composition further includes a pharmaceutically acceptable carrier, an excipient, a diluent, an adjuvant, a vehicle, or any combination thereof.

In a third aspect of the present disclosure, the present disclosure provides a use of the compound as described above or the pharmaceutical composition as described above in manufacture of a medicament for inhibiting osteoclast differentiation.

In a fourth aspect of the present disclosure, the present disclosure provides a use of the compound as described above or the pharmaceutical composition as described above in manufacture of a kit for inhibiting osteoclast differentiation.

In a fifth aspect of the present disclosure, the present disclosure provides a use of the compound as described above or the pharmaceutical composition as described above in manufacture of a medicament for treating or preventing osteoporosis or osteopenia.

The present disclosure has the following advantages and effects over the related art.

The hydrazone amide derivatives provided by the present disclosure can inhibit osteoclast differentiation to a certain extent, with good inhibitory activity and safety. The hydrazone amide derivatives provided by the present disclosure have a simple structure and are easy to be synthesized; and these compounds have low toxicity and can be safely used to prepare medicaments for the treatment and/or prevention of osteoporosis or osteopenia.

DESCRIPTION OF EMBODIMENTS

Figure 1:
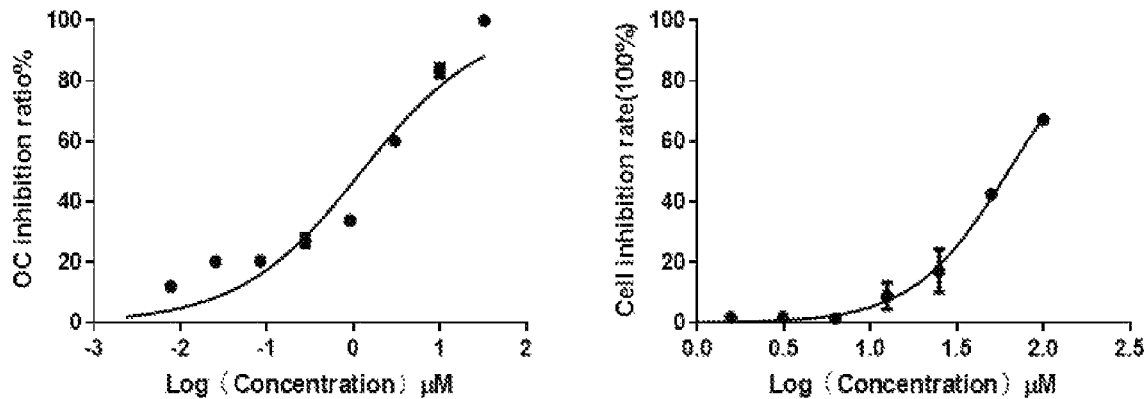
FIG. 1 illustrates an osteoclast differentiation inhibition curve and a RAW264.7-based cytotoxicity curve of Compound 1.

Embodiments of the present disclosure are described in detail below, and examples of the embodiments are shown in the accompanying drawings. The embodiments described below with reference to the accompanying drawings are illustrative, which aims to explain the present disclosure, but should not be interpreted as limiting the present disclosure.

The term "include" or "comprise" is an open-ended expression, i.e., including the content specified in the present disclosure but not excluding the content in other aspects.

"Stereoisomers" refer to compounds that have the same chemical structure but differ in the spatial arrangement of atoms or moieties. Stereoisomers include enantiomers, diastereomers, conformational isomers (rotamers), geometric isomers (cis/trans isomers), atropisomers, etc.

"Chirality" refers to a molecule that cannot overlap with its mirror image. "Achirality" refers to a molecule that can overlap with its mirror image.

"Enantiomers" refer to two isomers of a compound that are each a mirror image of the other one but cannot overlap with each other.

"Diastereomers" refer to stereoisomers that have two or more chiral centers and molecules of which are not mirror images of each other. Diastereomers have different physical properties such as melting point, boiling point, spectral properties and reactivity. A mixture of diastereomers can be separated by high-resolution analytical operations, for example, electrophoresis, and chromatography such as HPLC.

The definitions and rules of stereochemistry used in the present disclosure generally follow "McGraw-Hill Dictionary of Chemical Terms (1984)", S. P. Parker, Ed., McGraw-Hill Book Company, New York; and "Stereochemistry of Organic Compounds", Eliel, E. and Wilen, S., John Wiley & Sons, Inc., New York, 1994.

Many organic compounds exist in optically active forms, i.e., they are capable of rotating a plane of plane-polarized light. When describing optically active compounds, the prefixes D and L, or R and S are used to denote the absolute configurations of the molecule with respect to one or more chiral centers. The prefixes d and 1, or (+) and (−) are symbols used to specify a rotation of plane-polarized light caused by a compound, where (−) or 1 indicates that the compound is levorotatory, and the prefix (+) or d indicates that the compound is dextrorotatory. When specific stereoisomers are enantiomers, and a mixture of such isomers is called an enantiomeric mixture. A mixture of enantiomers in 50:50 is called a racemic mixture or a racemate, which may occur when there is no stereoselectivity or stereospecificity in a chemical reaction or process.

Any asymmetric atom (for example, carbon, etc.) of the compound of the present disclosure can be present in a racemate- or enantiomer-enriched form, for example, present in (R)-, (S)-, or (R, S)-configuration. In some embodiments, in terms of (R)- or (S)-configuration, each asymmetric atom has an enantiomeric excess of at least 50%, an enantiomeric excess of at least 60%, an enantiomeric excess of at least 70%, an enantiomeric excess of at least 80%, an enantiomeric excess of at least 90%, an enantiomeric excess of at least 95%, or an enantiomeric excess of at least 99%.

In accordance with the selection of starting materials and methods, the compounds of the present disclosure may be present as one of the possible isomers or a mixture thereof, such as a racemate and a mixture of diastereomers, depending on the number of asymmetric carbon atoms. The optically active (R)- or (S)-isomers can be prepared using chiral synthons or chiral reagents, or resolved using conventional techniques. If the compound contains a double bond, the substituent may be in the E or Z configuration; and if the compound contains disubstituted cycloalkyl, the substituent of the cycloalkyl may have a cis or trans configuration.

Any obtained mixture of stereoisomers can be separated into pure or substantially pure stereoisomers, enantiomers, diastereomers according to the differences in physical and chemical properties of components, for example, by chromatography and/or fractional crystallization process.

The racemate of the obtained end-product or intermediate can be resolved into optical enantiomers by methods known to those skilled in the art, for example, by separating the obtained diastereomeric salts. Racemic products can also be separated by chiral chromatography, such as high-performance liquid chromatography (HPLC) using chiral adsorbents. Particularly, the enantiomers can be prepared by asymmetric synthesis, for example, referring to "Enantiomers, Racemates and Resolutions", Jacques, et al., Wiley Interscience, New York, 1981; "Principles of Asymmetric Synthesis", $2^{nd}$ Ed. Robert E. Gawley, Jeffrey Aubé, Elsevier, Oxford, UK, 2012; "Stereochemistry of Carbon Compounds", Eliel, E. L., McGraw-Hill, N Y, 1962; "Tables of Resolving Agents and Optical Resolutions", p. 268, Wilen, S. H., E. L. Eliel, Ed., Univ. of Notre Dame Press, Notre Dame, in 1972; and "Chiral Separation Techniques: A Practical Approach", Subramanian, G. Ed., Wiley-VCH Verlag GmbH & Co. KGaA, Weinheim, Germany, 2007.

The term "tautomer" or "tautomeric form" refers to structural isomers that have different energies and can be interconverted by crossing a low energy barrier. If tautomerism is possible (for example, in solution), a chemical equilibrium of tautomers can be reached. For example, protontautomer (also known as prototropic tautomer) includes interconversion through proton migration, such as ketone-enol isomerization and imine-enamine isomerization. Valence tautomer includes interconversion through recombination of some bonding electrons. A specific example of ketone-enol tautomerization is interconversion of 2,4-pentanedione and 4-hydroxy-3-penten-2-one tautomeric isomers. Another example of tautomerism is phenol-ketone tautomerization. A specific example of phenol-ketone tautomerization is interconversion of 4-hydroxypyridine and pyridin-4(1H)-one tautomeric isomers. Unless otherwise indicated, all tautomeric forms of the compound of the present disclosure shall fall within the scope of the present disclosure.

In each part of the present specification, the substituents of the compounds disclosed in the present disclosure are disclosed according to the group types or ranges. In particular, the present disclosure includes each independent subcombination of respective members within these group types and ranges. For example, the term "$C_1$-$C_6$ alkyl" specifically refers to independently disclosed methyl, ethyl, $C_3$ alkyl, $C_4$ alkyl, $C_5$ alkyl, and $C_6$ alkyl.

In each part of the present disclosure, linking substituents are described. When the structure clearly requires a linking group, the Markush variables listed for the group should be understood as the linking group. For example, if the structure requires a linking group and the Markush group definition of the variable recites "alkyl" or "aryl", it should be understood that the "alkyl" or "aryl" respectively represents the linking alkylene group or arylene group.

As described in the present disclosure, the compounds of the present disclosure can be optionally substituted with one or more substituents, such as the compounds represented by the above general formulas, or particular examples, subclasses, and a type of compounds included in the present disclosure. It should be understood that the term "optionally substituted" and the term "substituted or unsubstituted" are interchangeably used. Generally speaking, the term "optionally", whether it precedes the term "substituted", means that one or more hydrogen atoms in a given structure may be substituted or unsubstituted by specific substituents. Unless otherwise indicated, an optionally substituted group may have a substituent substituted at each substitutable position of the group. When more than one position in the given structural formula can be substituted by one or more substituents selected from specific groups, the substituents substituted at the respective positions can be the same or different from each other.

The term "alkyl" used in the present disclosure includes linear or branched saturated monovalent hydrocarbyl group of 1-20 carbon atoms, where the alkyl can be independently and optionally substituted with one or more substituents described in the present disclosure. In some embodiments, the alkyl group contains 1-10 carbon atoms; in some other embodiments, the alkyl group contains 1-8 carbon atoms; in some other embodiments, the alkyl group contains 1-6 carbon atoms; in some other embodiments, the alkyl group contains 1-4 carbon atoms; in some other embodiments, the alkyl group contains 1-3 carbon atoms; and in some other embodiments, the alkyl group contains 2-6 carbon atoms. Further examples of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), 2-methylpropyl or isobutyl (i-Bu, —$CH_2CH(CH_3)_2$), 1-methylpropyl or sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl(-$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl(—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2, 3-dimethyl-2-butyl (—$C(CH_3)_2CH(CH_3)_2$), 3, 3-dimethyl-2-butyl (—$CH(CH_3)C(CH_3)_3$), n-heptyl, n-octyl, etc. The term "alkane group" and its prefix "alkane" used herein both include straight and branched saturated carbon chains.

The term "amino" refers to —$NH_2$.

The term "alkoxy" used in the present disclosure involves alkyl, as defined in the present disclosure, connected to a main carbon chain through an oxygen atom. Such examples include, but are not limited to, methoxy, ethoxy, propoxy, and the like.

The term "cycloalkyl" refers to a monovalent or multivalent saturated monocyclic, bicyclic or tricyclic ring system containing 3-12 carbon atoms. The bicyclic or tricyclic ring system may include fused rings, bridged rings, and spiro rings. In an embodiment, cycloalkyl contains 3-10 carbon atoms; in another embodiment, cycloalkyl contains 3-8 carbon atoms; in another embodiment, cycloalkyl contains 3-6 carbon atoms. Examples of cycloalkyl include, but are not limited to, cyclopropyl, cyclobutyl, cyclopentyl, cyclohexyl, and the like. The cycloalkyl group is optionally substituted with one or more substituents described in the present disclosure.

The term "aryl" refers to a monocyclic, bicyclic and tricyclic carbon ring system containing 6-14 ring atoms, or 6-12 ring atoms, or 6-10 ring atoms, at least one ring of which is aromatic. The aryl group is usually, but not necessarily, connected to the core moiety through the aromatic ring of the aryl group. The term "aryl" can be used interchangeably with the term "aromatic ring". Examples of the aryl may include phenyl, naphthyl, and anthranyl. The aryl group is optionally substituted with one or more substituents described in the present disclosure.

The term "heteroaromatic ring" refers to a monocyclic, bicyclic and tricyclic ring system containing 5-12 ring atoms, or 5-10 ring atoms, or 5-6 ring atoms, at least one ring of which is aromatic and at least one ring of which contains one or more heteroatoms. The heteroaromatic ring is usually, but not necessarily, connected to the core moiety through the aromatic ring of the heteroaromatic ring. The term "heteroaryl" can be used interchangeably with the term "heteroaromatic ring", "aromatic heterocyclic ring" or "heteroaromatic compound". The heteroaryl group is optionally substituted with one or more substituents described in the present disclosure. In an embodiment, the heteroaryl group, consisting of 5 to 10 atoms, contains 1, 2, 3, or 4 heteroatoms independently selected from O, S, or N.

Examples of the heteroaryl include, but are not limited to, 2-furyl, 3-furyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (such as 3-pyridazinyl), 2-thiazolyl, 4-thiazolyl, 5-thiazolyl, tetrazolyl (such as 5-tetrazolyl), triazolyl (such as 2-triazolyl and 5-triazolyl), 2-thienyl, 3-thienyl, pyrazolyl (such as 2-pyrazolyl), isothiazolyl, 1,2,3-oxadiazolyl, 1,2,5-oxadiazolyl, 1,2,4-oxadiazolyl, 1,2,3-triazolyl, 1,2,3-thiodiazolyl, 1,3,4-thiodiazolyl, 1,2,5-thiodiazolyl, pyrazinyl, 1,3,5-triazinyl. Examples of heteroaryl further include, but not limited to, the following bicyclic rings: benzimidazolyl, benzofuranyl, benzothienyl, indolyl (such as 2-indolyl), purinyl, quinolinyl (such as 2-quinolinyl, 3-quinolinyl, 4-quinolinyl), isoquinolinyl (such as 1-isoquinolinyl, 3-isoquinolinyl or 4-isoquinolinyl), imidazo[1,2-a]pyridinyl, pyrazolo[1,5-a]pyridyl, pyrazolo[1,5-a]pyrimidinyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, etc.

As described in the present disclosure, a ring system with a substituent R' connected to a core ring of the ring system through one bond represents that the substituent R' can be substituted at any substitutable or any suitable position on the ring. For example, formula a represents that any substitutable position on the B' ring can be substituted with R', e.g., shown in formula b, formula c and formula d.

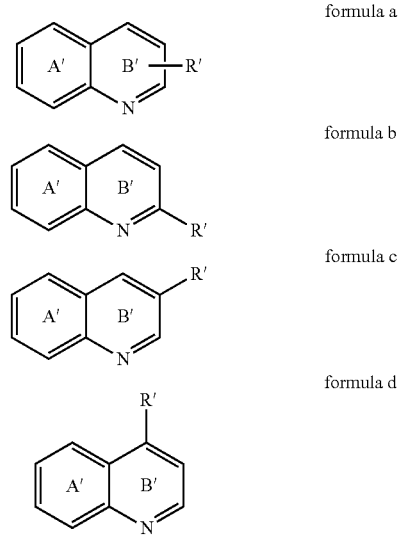

formula a formula b formula c formula d

In addition, it should be noted that, unless explicitly stated otherwise, the expressions used throughout the present disclosure such as "each of . . . and . . . is independently", " . . . and . . . are each independently" and " . . . and . . . are respectively independently" are interchangeable and should be understood in a broad sense. They mean that in different groups, the specific options expressed by the same symbols do not affect each other; or in the same group, the specific options expressed by the same symbols do not affect each other. For example, in "—$(C(R^7)_2)_{n1}$—$NR^8$—$(C(R^7)_2)_{n1}$—", the specific options of each $R^7$ can be the same or different, and the expressed specific items can also be the same or different; the specific options of each n1 can be the same or different, and the expressed specific items can also be the same or different. Further, for example, in formula (I), the specific options of each of $R^2$, $R^3$ or $R^4$ may be the same or different, and the specific items expressed by $R^2$, $R^3$ and $R^4$ may also be the same or different.

The term "pharmaceutically acceptable" refers to molecular entities and compositions that are physiologically tolerable when administered to humans and generally do not produce allergies or similar inappropriate reactions, such as gastrointestinal discomfort, dizziness, and the like. Preferably, the term "pharmaceutically acceptable" as used herein refers to those approved by a federal regulatory agency or a national government or recorded in the US Pharmacopoeia or other generally recognized pharmacopoeia for use in animals, more particularly in humans.

The term "carrier" refers to a diluent, adjuvant, excipient or matrix that is administered together with the compound. These pharmaceutical carriers can be sterile liquids such as water and oils, including those derived from petroleum, animals, plants, or synthetic sources, such as peanut oil, soybean oil, mineral oil, sesame oil, and the like. Water, aqueous saline solution, aqueous dextrose, and glycerite are preferably used as carriers, especially for injectable solutions. Suitable carriers of medicaments are described in "Remington's Pharmaceutical Sciences", by E. W. Martin.

The "hydrate" of the present disclosure refers to the compound or its salt provided by the present disclosure with chemical or non-chemical equivalent water bonded thereto by non-covalent intermolecular force, i.e., an associated complex formed when the solvent molecule is water.

The "solvate" of the present disclosure refers to an associated complex formed by one or more solvent molecules and the compound of the present disclosure. The solvents for forming the solvate include, but are not limited to, water, isopropanol, ethanol, methanol, dimethyl sulfoxide, ethyl acetate, acetic acid, and aminoethanol.

The "nitrogen oxide" of the present disclosure means that, when the compound contains several amine functional groups, one or more nitrogen atoms can be oxidized to form N-oxide. Specific examples of N-oxides are N-oxides of tertiary amines or N-oxides of the nitrogen atom of nitrogen heterocycle. An oxidant such as hydrogen peroxide or peracid (such as peroxycarboxylic acid) can be used to process a corresponding amine to form N-oxide (see Advanced Organic Chemistry, Wiley Interscience, 4th edition, Jerry March, pages). In particular, N-oxides can be prepared by the method by L. W. Deady (Syn. Comm. 1977, 7, 509-514), in which, for example, the amine compound reacts with m-chloroperoxybenzoic acid (MCPBA) in an inert solvent such as dichloromethane.

The term "prodrug" used in the present disclosure indicates a compound that is converted into a compound represented by formula (I) in vivo. Such conversion is affected by a prodrug hydrolysis in blood or an enzymatic conversion into a parent structure in blood or tissues. The prodrug compounds of the present disclosure may be esters. In the present disclosure, the esters serving as prodrugs include phenyl esters, aliphatic ($C_{1-24}$) esters, acyloxymethyl esters, carbonate esters, carbamate esters and amino acid esters. For example, a compound in the present disclosure contains hydroxyl, which can be acylated to obtain a compound in the form of a prodrug. Other forms of the prodrug include phosphate esters, for example, the phosphate ester compounds obtained by phosphorylation of the hydroxyl group on the parent structure. For a full discussion of prodrugs, please refer to the following literatures: T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345.

All tautomeric forms of the compounds of the present disclosure are included in the scope of the present disclosure, unless otherwise indicated.

In addition, the structural formulas of the compounds described in the present disclosure include enriched isotopes of one or more different atoms, unless otherwise indicated. The present disclosure includes isotopically-labeled compounds, which are equivalent to the compounds represented by formula (I), but one or more atoms thereof are replaced by atoms with atomic mass or mass number different from the common atomic mass or mass number in nature. Examples of isotopes that can be introduced in the compounds of the present disclosure include isotopes of hydrogen, carbon, nitrogen, oxygen, phosphorus, sulfur, fluorine, and chlorine, such as $^{2}H$, $^{3}H$, $^{13}C$, $^{11}C$, $^{14}C$, $^{14}C$, $^{15}N$, $^{18}O$, $^{17}O$, $^{31}P$, $^{32}P$, $^{35}S$, $^{18}F$ and $^{36}Cl$. The compounds of the present disclosure containing the above isotopes and/or other isotopes of other atoms, prodrugs thereof, and pharmaceutically acceptable salts of the compounds or the prodrugs all fall within the scope of the present disclosure. The isotopically-labeled compounds of formula (I) of the present disclosure and their prodrugs can generally be prepared in this way: when performing the following procedures and/or the processes disclosed in the examples and preparation examples, the non-isotopically labeled reagents are replaced by the isotopically-labeled reagents that are easily available.

"Metabolite" refers to a product obtained by metabolizing a specific compound or its salt in vivo. The metabolite of one compound can be identified by techniques well known in the art, and its activity can be characterized by assays as described in the present disclosure. Such a product may be obtained through oxidation, reduction, hydrolysis, amidation, deamidation, esterification, de-esterification, or enzyme cleavage of the administrated compound, or the like. Accordingly, the present disclosure includes the metabolites of the compound, including metabolites produced by fully contacting the compound of the present disclosure with a mammal for a period of time.

Various pharmaceutically acceptable salt forms of the compounds of the present disclosure are useful. The term "pharmaceutically acceptable salts" refers to the salt forms that are apparent to pharmaceutical chemists, that is, they are substantially non-toxic and can provide the desired pharmacokinetic properties, palatability, absorption, distribution, metabolism or excretion. Other factors, which are more practical in terms of properties and are also important in terms of selection, include: the cost of raw materials, ease of crystallization, yield, stability, hygroscopicity, and fluidity of the resulting crude drugs. In brief, the pharmaceutical composition can be prepared from an active component and a pharmaceutically acceptable carrier.

As used herein, a "pharmaceutically acceptable salt" refers to an organic or inorganic salt of the compound of the present disclosure. The pharmaceutically acceptable salts are well known in the art, as described in the literature: S. M. Berge et al., describe pharmaceutically acceptable salts in detail in J. Pharmaceutical Sciences, 66: 1-19, 1977. Salts formed by pharmaceutically acceptable non-toxic acids include, but are not limited to, inorganic acid salts formed by reacting with amino groups, including hydrochloride, hydrobromide, phosphate, sulfate, perchlorate, nitrate, etc; and organic acid salts such as acetate, propionate, glycollate, oxalate, maleate, malonate, succinate, fumarate, tartrate, citrate, benzoate, mandelate, methanesulfonate, ethanesulfonate, tosylate, sulfosalicylate, etc., or the salts obtained through other methods such as ion exchange described in book literatures.

Other pharmaceutically acceptable salts include adipate, malate, 2-hydroxypropionic acid, alginate, ascorbate, aspartate, benzenesulfonate, benzoate, bisulfate, borate, butyrate, camphorate, camphorsulfonate, cyclopentylpropionate, digluconate, dodecyl sulfate, esilate, formate, fumarate, gluceptate, glycerophosphate, gluconate, hemisulphate, enanthate, caproate, hydriodate, 2-hydroxy-ethanesulfonate, lactobionic acid salt, lactate, laurate, lauryl sulfate, malate, malonate, methanesulfonate, 2-naphthalenesulfonate, nicotinate, nitrate, oleate, palmitate, pamoate, pectate, persulfate, 3-phenylpropionate, picrate, pivalate, propionate, stearate, thiocyanate, p-toluene sulfonate, undecanoate, valerate, etc. Salts obtained from suitable bases include salts of alkali metal, alkaline earth metal, ammonium, and $N^{+}(C_{1-4}\text{ alkyl})_{4}$.

The present disclosure also contemplates quaternary ammonium salts formed by any compound with a group containing N. Water-soluble or oil-soluble or dispersed products can be obtained by quaternization. The salts of alkali metal or alkaline earth metal include sodium salts, lithium salts, potassium salts, calcium salts, magnesium salts, iron salts, zinc salts, copper salts, manganese salts, aluminum salts, etc. The pharmaceutically acceptable salts further include suitable and non-toxic ammoniums, quaternary ammonium salts and amine cations formed by counterions, such as halides, hydroxides, carboxylates, hydrosulfates, phosphates, nitrates, $C_{1-8}$ sulfonates and aromatic sulfonates. The ammonium salts, such as but not limited to N, N'-dibenzylethylenediamine, chloroprocaine, choline, ammonia, diethanolamine and other hydroxyalkylamines, ethylenediamine, N-methyl glucosamine, procaine, N-benzylphenethylamine, 1-p-chlorobenzyl-2-pyrrolidine-1'-ylmethyl-benzimidazole, diethylamine and other alkylamines, piperazine, and tris(hydroxymethyl)aminomethane; alkaline earth metal salts, such as but not limited to barium, calcium and magnesium; transition metal salts, for example, including, but not limited to zinc.

In this specification, the structure shall prevail if the chemical name is different from the chemical structure.

Unless otherwise specified, the abbreviations of any amino acids and other compounds used in the present disclosure are the commonly used and recognized abbreviations, or refer to IUPAC-IUB Commission on Biochemical Nomenclature (see Biochem. 1972, 11: 942-944).

A first aspect of the present disclosure provides a new compound having significant osteoclast inhibitory activity.

A second aspect of the present disclosure provides a new compound that can significantly treat or prevent osteoporosis or osteopenia.

A third aspect of the present disclosure provides a method for preparing the osteoclast inhibiting compound.

A fourth aspect of the present disclosure provides use of the compound in the treatment or prevention of osteoporosis or osteopenia.

The compound provided by the present disclosure has significant osteoclast-inhibiting activity and can serve as a lead compound for the treatment or prevention of osteoporosis or osteopenia.

The present disclosure will be further described below with reference to specific embodiments and drawings. However, the embodiments do not limit the present disclosure in any form. The reagents, methods and devices used in the present disclosure are conventional reagents, methods and devices in the art, unless otherwise specified.

Unless otherwise specified, the reagents and materials used in the present disclosure are all commercially available.
The compounds to be synthesized in the following examples are shown below.
1
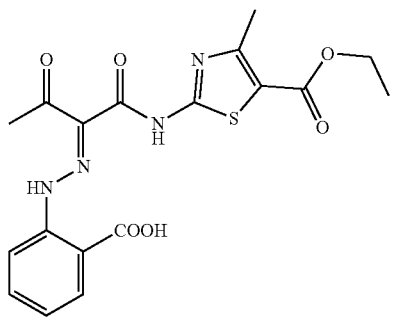
2
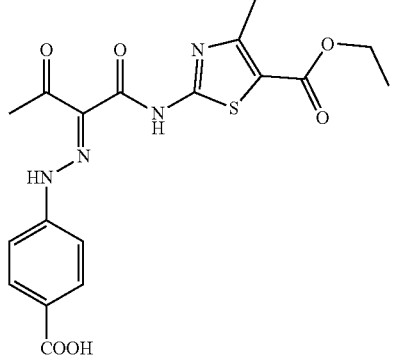
3
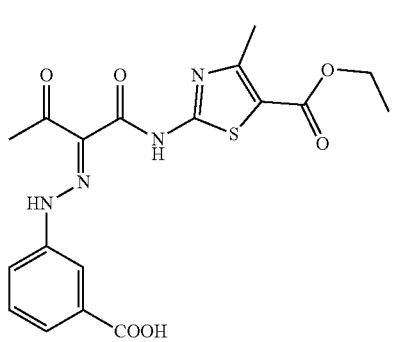
4
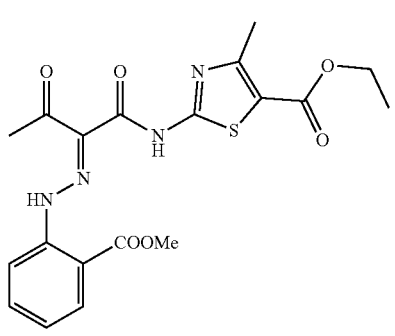
-continued
5
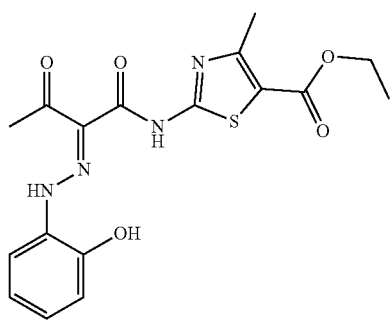
6
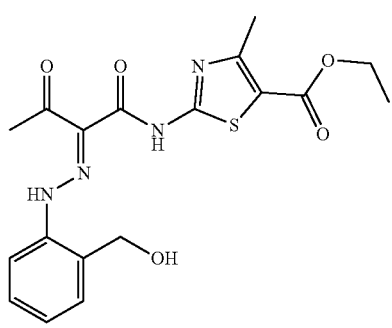
7
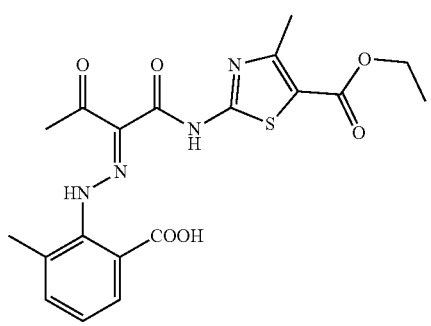
8
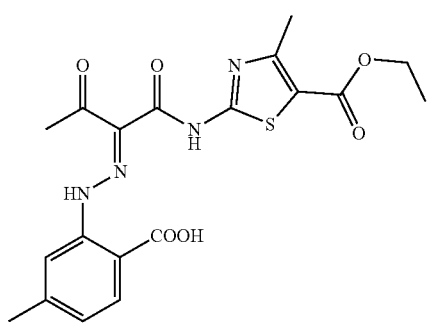
9
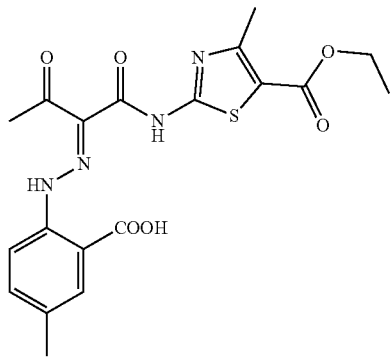

10 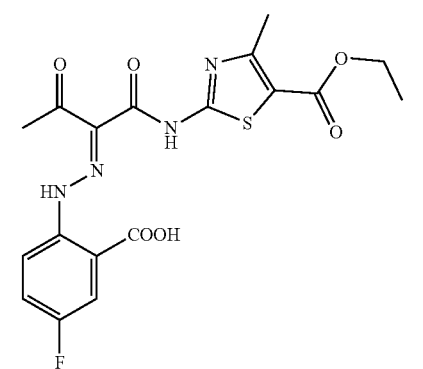
11 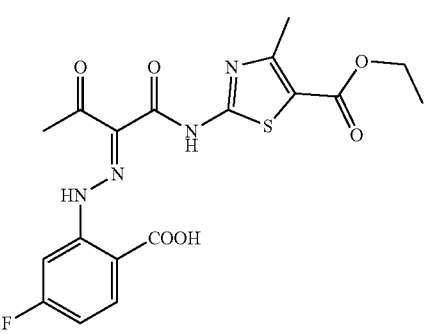
12 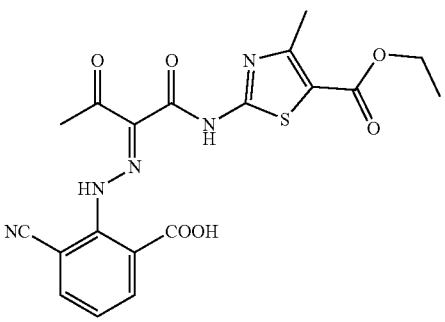
13 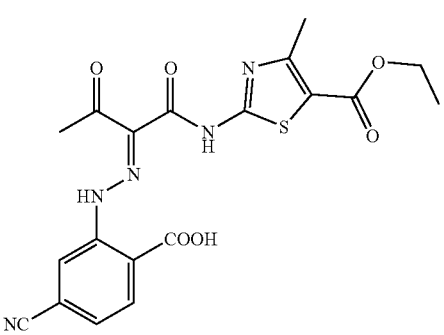
14 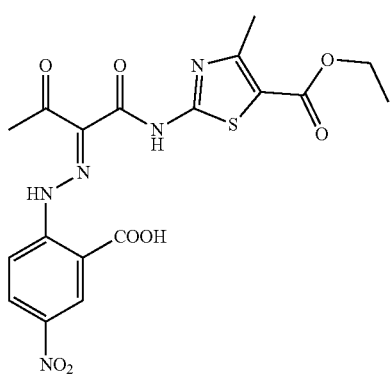
15 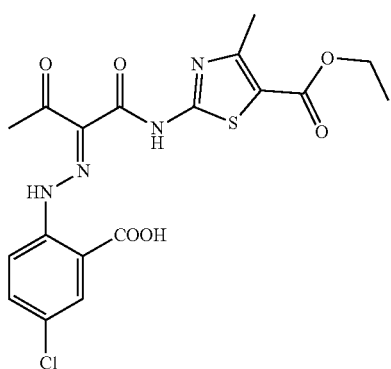
16 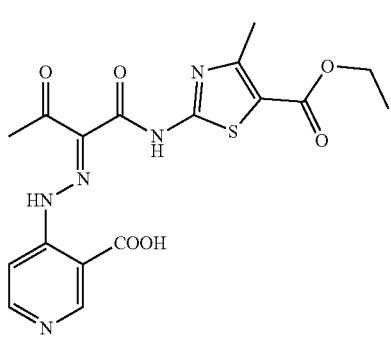
17 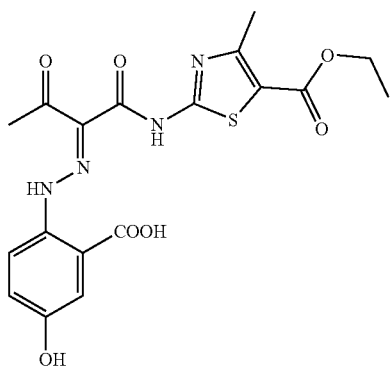

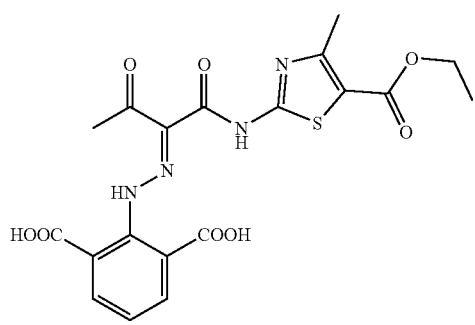
18
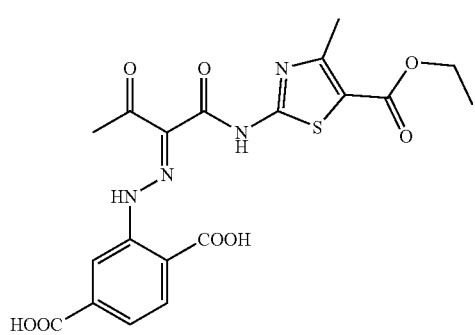
19
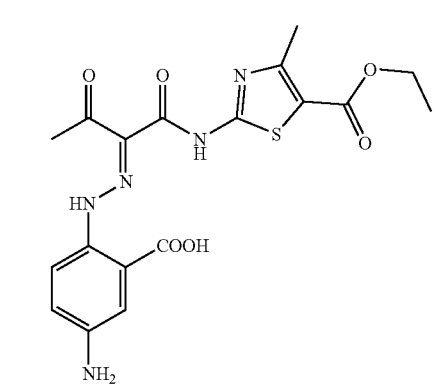
20
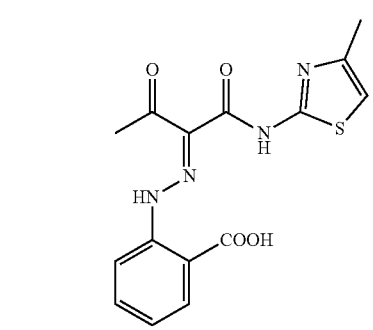
21
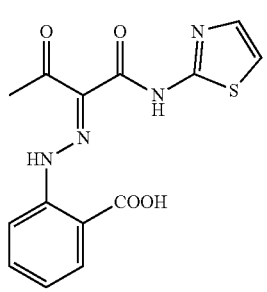
22
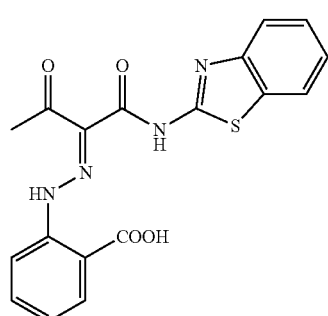
23
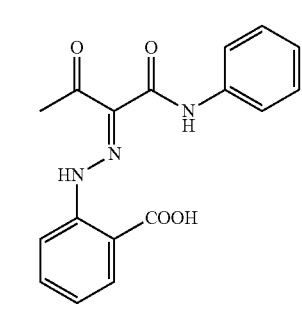
24
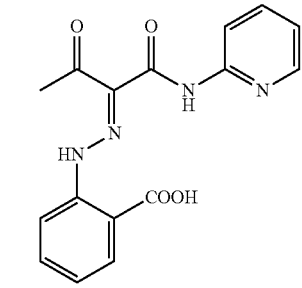
25
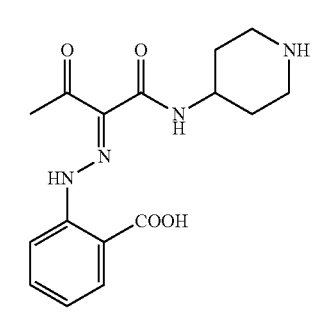
26
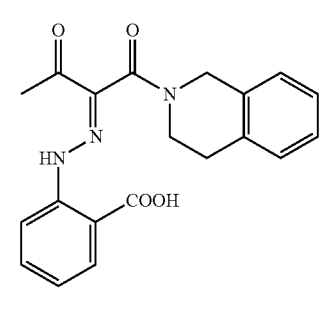
27

-continued

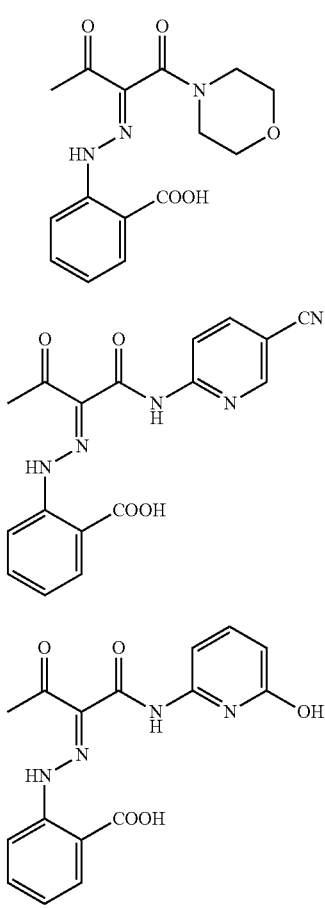

Example 1: Synthesis of Hydrazone Amide Derivatives

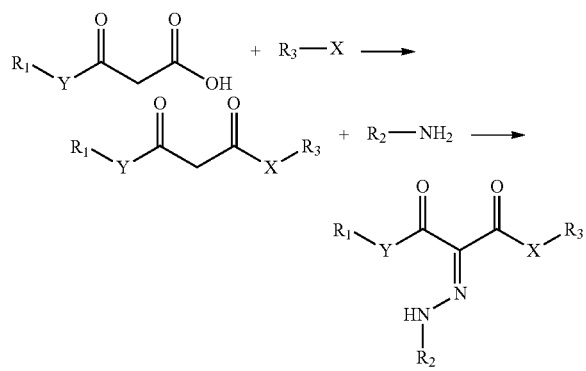

The synthesis scheme of hydrazone amide derivatives is illustrated as above.

Substituted acetoacetic acid, 1,3-dicyclohexylcarbodiimide (DCC), 4-dimethylaminopyridine (DMAP), and substituted alcohol or ammonia were added into dichloromethane, and stirred for 8 h at room temperature. The solvent was removed using a rotary evaporator, and the corresponding acetoacetamide or acetoacetate was obtained after purifying with column chromatography.

Ammonias with different substituents were added to methanol, and hydrochloric acid and sodium nitrite in equal amounts were added and stirred at room temperature for 0.5 hours. Then, the substituted acetoacetamide or acetoacetate was added and stirred at room temperature for 10 hours, and the desired hydrazone amide derivatives were obtained after filtering.

Example 2: Synthesis of Compound 1

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 70 mg of 2-aminobenzoic acid reacted together to obtain 150 mg of Compound 1, with a yield of 72%.

Example 3: Synthesis of Compound 2

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 70 mg of 4-aminobenzoic acid reacted together to obtain 160 mg of Compound 2, with a yield of 77%.

Example 4: Synthesis of Compound 3

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 70 mg of 3-aminobenzoic acid reacted together to obtain 141 mg of Compound 3, with a yield of 67%.

Example 5: Synthesis of Compound 4

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 75 mg of methyl 2-aminobenzoate reacted together to obtain 187 mg of Compound 4, with a yield of 86%.

Example 6: Synthesis of Compound 5

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 54 mg of 2-aminophenol reacted together to obtain 103 mg of Compound 5, with a yield of 53%.

Example 7: Synthesis of Compound 6

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 62 mg of 2-aminobenzyl alcohol reacted together to obtain 155 mg of Compound 6, with a yield of 77%.

Example 8: Synthesis of Compound 7

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 76 mg of 2-amino-3-methylbenzoic acid reacted together to obtain 124 mg of Compound 7, with a yield of 57%.

Example 9: Synthesis of Compound 8

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 76 mg of 2-amino-4-methylbenzoic acid reacted together to obtain 132 mg of Compound 8, with a yield of 61%.

Example 10: Synthesis of Compound 9

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 76 mg of 2-amino-5-methyl-benzoic acid reacted together to obtain 105 mg of Compound 9, with a yield of 49%.

Example 11: Synthesis of Compound 10

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 77 mg of 2-amino-5-fluorobenzoic acid reacted together to obtain 108 mg of Compound 10, with a yield of 50%.

Example 12: Synthesis of Compound 11

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 77 mg of 2-amino-4-fluorobenzoic acid reacted together to obtain 136 mg of Compound 11, with a yield of 62%.

Example 13: Synthesis of Compound 12

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 81 mg of 2-amino-3-cyanobenzoic acid reacted together to obtain 92 mg of Compound 12, with a yield of 41%.

Example 14: Synthesis of Compound 13

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 76 mg of 2-amino-4-cyanobenzoic acid reacted together to obtain 172 mg of Compound 13, with a yield of 78%.

Example 15: Synthesis of Compound 14

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 91 mg of 2-amino-5-nitrobenzoic acid reacted together to obtain 167 mg of Compound 14, with a yield of 72%.

Example 16: Synthesis of Compound 15

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 85 mg of 2-amino-5-chlorobenzoic acid reacted together to obtain 179 mg of Compound 15, with a yield of 79%.

Example 17: Synthesis of Compound 16

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 70 mg of 4-amino-5-pyridinedicarboxylic acid reacted together to obtain 164 mg of Compound 16, with a yield of 79%.

Example 18: Synthesis of Compound 17

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 76 mg of 4-amino-5-hydroxylbenzoic acid reacted together to obtain 133 mg of Compound 17, with a yield of 61%.

Example 19: Synthesis of Compound 18

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 91 mg of 2-aminoisophthalic acid reacted together to obtain 111 mg of Compound 18, with a yield of 48%.

Example 20: Synthesis of Compound 19

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 91 mg of 2-aminoterephthalic acid reacted together to obtain 141 mg of Compound 19, with a yield of 61%.

Example 21: Synthesis of Compound 20

According to the procedure described in Example 1, 186 mg of ethyl 2-amino-4-methylthiazole-5-carboxylate, 206 mg of DCC, 10 mg of DMAP, and 102 mg of 3-oxobutyric acid reacted together to obtain 200 mg of ethyl-4-methyl-2-acetoacetylthiazolamide-5-carboxylate, with a yield of 74%.

135 mg of ethyl-4-methyl-2-acetoacetylthiazolamide-5-carboxylate, 0.5 ml of hydrochloric acid (1M), 34 mg of sodium nitrite, and 76 mg of 2, 5-diaminobenzoic acid reacted together to obtain 130 mg of Compound 20, with a yield of 62%.

Example 22: Synthesis of Compound 21

According to the procedure described in Example 1, 114 mg of 2-amino-4-methylthiazole, 206 mg of DCC, 10 mg of DMAP, and 102 mg of 3-oxobutyric acid reacted together to obtain 185 mg of 4-methyl-2-acetoacetylthiazolamide, with a yield of 93%.

100 mg of 4-methyl-2-acetoacetylthiazolamide, 0.5 ml of hydrochloric acid (1M), 34 mg of sodium nitrite, and 70 mg of 2-aminobenzoic acid reacted together to obtain 102 mg of Compound 21, with a yield of 59%.

Example 23: Synthesis of Compound 22

As described in Example 1, 100 mg of 2-aminothiazole, 206 mg of DCC, 10 mg of DMAP, and 102 mg of 3-oxobutyric acid reacted together to obtain 139 mg of 2-acetoacetylthiazolamide, with a yield of 76%.

91 mg of 2-acetoacetylthiazolamide, 0.5 ml of hydrochloric acid (1M), 34 mg of sodium nitrite, and 70 mg of 2-aminobenzoic acid reacted together to obtain 102 mg of Compound 22, with a yield of 59%.

Example 24: Synthesis of Compound 23

According to the procedure described in Example 1, 150 mg of 2-amino-benzothiazole, 206 mg of DCC, 10 mg of DMAP, and 102 mg of 3-oxobutyric acid reacted together to obtain 158 mg of 2-acetoacetylbenzothiazolamide, with a yield of 68%.

116 mg of 2-acetoacetylbenzothiazolamide, 0.5 ml of hydrochloric acid (1M), 34 mg of sodium nitrite, and 70 mg of 2-aminobenzoic acid reacted together to obtain 117 mg of Compound 23, with a yield of 61%.

Example 25: Synthesis of Compound 24

According to the procedure described in Example 1, 92 mg of aniline, 206 mg of DCC, 10 mg of DMAP, and 102 mg of 3-oxobutyric acid reacted together to obtain 125 mg of acetoacetanilide, with a yield of 71%.

88 mg of acetoacetanilide, 0.5 ml of hydrochloric acid (1M), 34 mg of sodium nitrite, and 70 mg of 2-aminobenzoic acid reacted together to obtain 97 mg of Compound 24, with a yield of 59%.

Example 26: Synthesis of Compound 25

According to the procedure described in Example 1, 93 mg of 2-aminopyridine, 206 mg of DCC, 10 mg of DMAP, and 102 mg of 3-oxobutyric acid reacted together to obtain 104 mg of 2-acetoacetpyridinamine, with a yield of 59%.

88 mg of 2-acetoacetpyridinamine, 0.5 ml of hydrochloric acid (1M), 34 mg of sodium nitrite, and 70 mg of 2-aminobenzoic acid reacted together to obtain 85 mg of Compound 25, with a yield of 52%.

Example 27: Synthesis of Compound 26

According to the procedure described in Example 1, 99 mg of 4-aminopiperidine, 206 mg of DCC, 10 mg of DMAP, and 102 mg of 3-oxobutyric acid reacted together to obtain 128 mg of 3-oxo-N-piperidine-4-butanamide, with a yield of 70%.

91 mg of 3-oxo-N-piperidine-4-butanamide, 0.5 ml of hydrochloric acid (1M), 34 mg of sodium nitrite, and 70 mg of 2-aminobenzoic acid reacted together to obtain 75 mg of Compound 26, with a yield of 45%.

Example 28: Synthesis of Compound 27

According to the procedure described in Example 1, 133 mg of tetrahydroisoquinoline, 206 mg of DCC, 10 mg of DMAP, and 102 mg of 3-oxobutyric acid reacted together to obtain 129 mg of 1-tetrahydroisoquinolinebutyl-1,3-dione, with a yield of 60%.

108 mg of 1-tetrahydroisoquinolinebutyl-1,3-dione, 0.5 ml of hydrochloric acid (1M), 34 mg of sodium nitrite, and 70 mg of 2-aminobenzoic acid reacted together to obtain 86 mg of Compound 27, with a yield of 47%.

Example 29: Synthesis of Compound 28

According to the procedure described in Example 1, 88 mg of morpholine, 206 mg of DCC, 10 mg of DMAP, and 102 mg of 3-oxobutyric acid reacted together to obtain 106 mg of acetoacetylmorpholinylamine, with a yield of 63%.

85 mg of acetoacetylmorpholinylamine, 0.5 ml of hydrochloric acid (1M), 34 mg of sodium nitrite, and 70 mg of 2-aminobenzoic acid reacted together to obtain 89 mg of Compound 28, with a yield of 56%.

Example 30: Synthesis of Compound 29

According to the procedure described in Example 1, 119 mg of 2-amino-5-cyanopyridine, 206 mg of DCC, 10 mg of DMAP, and 102 mg of 3-oxobutyric acid reacted together to obtain 137 mg of 5-cyanopyridine-2-acetoacetamide, with a yield of 67%.

101 mg of 5-cyanopyridine-2-acetoacetamide, 0.5 ml of hydrochloric acid (1M), 34 mg of sodium nitrite, and 70 mg of 2-aminobenzoic acid reacted together to obtain 88 mg of Compound 29, with a yield of 50%.

Example 31: Synthesis of Compound 32

According to the procedure described in Example 1, 110 mg of 2-amino-6-hydroxylpyridine, 206 mg of DCC, 10 mg of DMAP, and 102 mg of 3-oxobutyric acid reacted together to obtain 160 mg of 6-hydroxylpyridine-2-acetoacetamide, with a yield of 83%.

96 mg of 6-hydroxylpyridine-2-acetoacetamide, 0.5 ml of hydrochloric acid (1M), 34 mg of sodium nitrite, and 70 mg of 2-aminobenzoic acid reacted together to obtain 106 mg of Compound 30, with a yield of 62%.

Example 32: Cytotoxicity Assay of Compounds

S1. Cell Culturing

RAW264.7 cells were cultured in vitro using DMEM high glucose medium containing 10% fetal bovine serum at 37° C. under 5% $CO_2$ for routine maintenance culture and passage.

S2. Compound Intervention

The logarithmic growth phase cells were collected and formulated into a cell suspension at a concentration of $1\times10^5$ cells/mL, and the cell suspension was added to a 96-well cell culture plate. After culturing in a carbon dioxide incubator for 24 hours, the culture medium was replaced with a medium containing the compound at different concentrations to continue culturing for 2 days, and the cytotoxicity was detected on day 3. The compound to be tested was prepared into solutions of different concentrations using DMSO. Three wells were set for each concentration, and a control group without the compound treatment was set for comparison.

S3. Test Method

MTT (3-(4,5-dim ethyl-2-thiazolyl)-2,5-diphenyl-2H-tetrazoliumbromide) method was used to test the cells that had been treated with the compound for 6 days. the absorbance value (OD value) of each well was measured using a microplate reader (detection wavelength 570 nm, reference wavelength 630 nm).

S4. Processing of Results

The RAW264.7 cell growth inhibition rate by each compound was calculated according to the following equation:

$$\text{Cell growth inhibition rate} = \frac{OD \text{ value of well with control cells} - OD \text{ value of well with treated cells}}{OD \text{ value of well with control cells}} \times 100\%$$

A cell growth inhibition curve of each compound was plotted with the RAW264.7 cell growth inhibition rate as the ordinate and the logarithm of the compound concentration as the abscissa. According to the inhibition rate of each compound on the cells, the 50% cytotoxic concentration $CC_{50}$ was calculated, i.e., the concentration of the compound that is required for 50% inhibition of cell growth.

In addition, a selective inhibition constant of each compound was calculated according to the equation: selective inhibition constant $(SI)=CC_{50}/IC_{50}$, in order to evaluate the administration safety of each compound. The results of selective inhibition constants of all compounds are shown in Table 1.

Example 33: Osteoclast Differentiation Inhibition Experiment

S1. Cell Culturing

RAW264.7 cells were cultured in vitro using DMEM high glucose medium containing 10% fetal bovine serum at 37° C. under 5% $CO_2$ for routine maintenance culture and passage.

S2. Compound Intervention

The logarithmic growth phase cells were collected and formulated into a cell suspension at a concentration of $2\times10^4$ cells/mL, and the cell suspension were added to a 96-well cell culture plate. After culturing in a carbon dioxide incubator for 24 hours, the culture medium was replaced with a medium containing 100 ng/ml RANKL and the compound at different concentrations to continue culturing for 5 days, while changing the medium containing the same RANKL concentration and compound concentration every 2 days. The osteoclasts were stained with the TRAP staining method and measured on day 5. Three wells were set for each concentration, and a control group without the compound treatment was set for comparison.

S3. Test Method

The differentiated osteoclasts were stained with TRAP kit, and the number of osteoclasts fused by 3 or more nuclei was counted.

S4. Processing of Results

The inhibition rate of each compound on RANKL-induced osteoclast differentiation was calculated according to the following equation:

$$\text{Osteoclast inhibition rate} = \frac{RANKL\text{-induced osteoclast count} - \text{compound-intervened osteoclast count}}{RANKL\text{-induced osteoclast count}} \times 100$$

An osteoclast differentiation inhibition curve of each compound was plotted with the osteoclast differentiation inhibition rate as the ordinate and the logarithm of the compound concentration as the abscissa. According to the osteoclast differentiation inhibition rate by each compound, the half maximal inhibitory concentration $IC_{50}$ was calculated, i.e., the concentration of the compound that is required for 50% osteoclast differentiation inhibition.

In addition, a selective inhibition constant of each compound was calculated according to the equation: selective inhibition constant $(SI)=CC_{50}/IC_{50}$, in order to evaluate the administration safety of each compound.

Based on the value of the selective index $SI=CC_{50}/IC_{50}$, the anti-osteoporotic differentiation effect of the compound was evaluated according to the following criteria. $SI<1.0$ indicates that the compound is toxic and ineffective; $1.0 \leq SI \leq 2.0$ indicates that the compound is inefficient and toxic, i.e., weakly positive; $2.0<SI<10.0$ indicates that the compound is effective and has low toxicity, i.e., positive; and $SI \geq 10.0$ indicates that the compound is highly effective and has low toxicity, i.e., strong positive.

Figure 2:
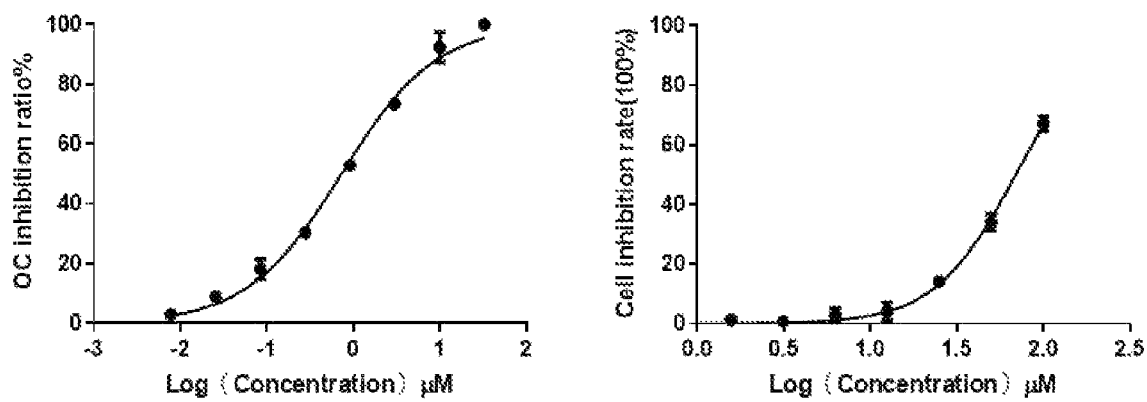
FIG. 2 illustrates an osteoclast differentiation inhibition curve and a RAW264.7-based cytotoxicity curve of Compound 2.
Figure 3:
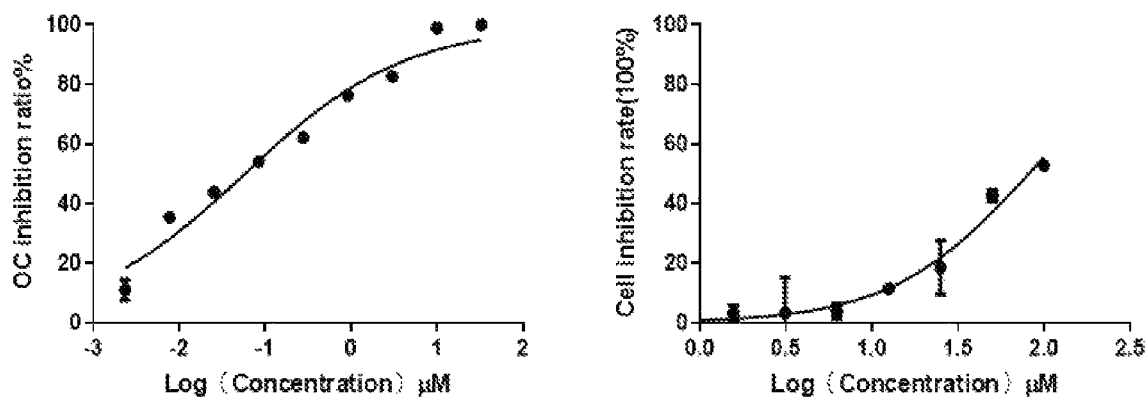
FIG. 3 illustrates an osteoclast differentiation inhibition curve and a RAW264.7-based cytotoxicity curve of Compound 3.
Figure 4:
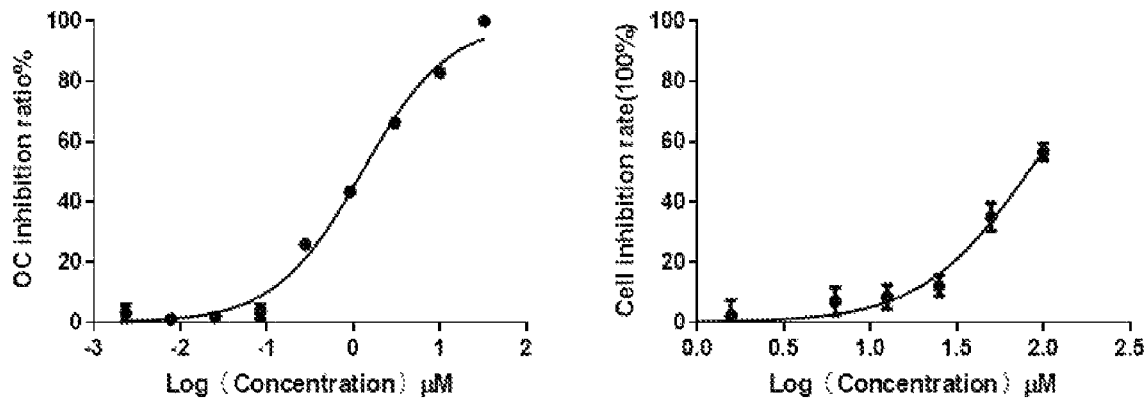
FIG. 4 illustrates an osteoclast differentiation inhibition curve and a RAW264.7-based cytotoxicity curve of Compound 4.
Figure 5:
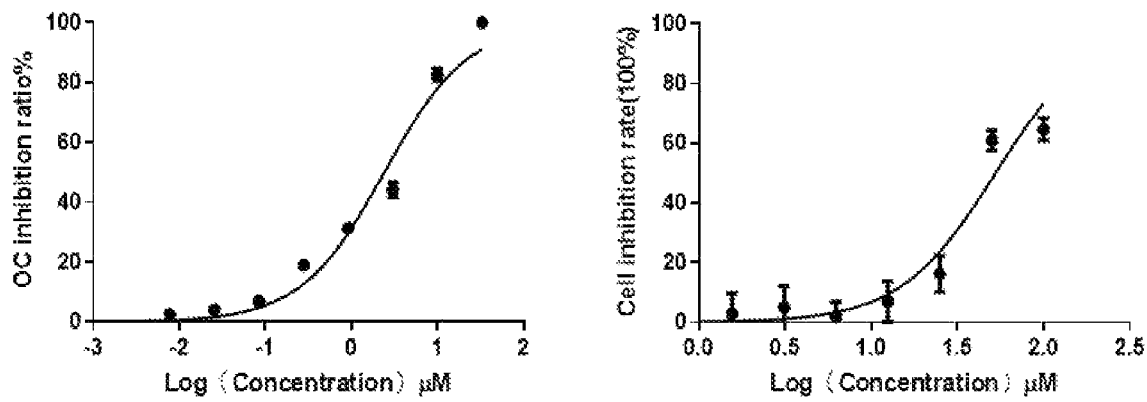
FIG. 5 illustrates an osteoclast differentiation inhibition curve and a RAW264.7-based cytotoxicity curve of Compound 5.
Figure 6:
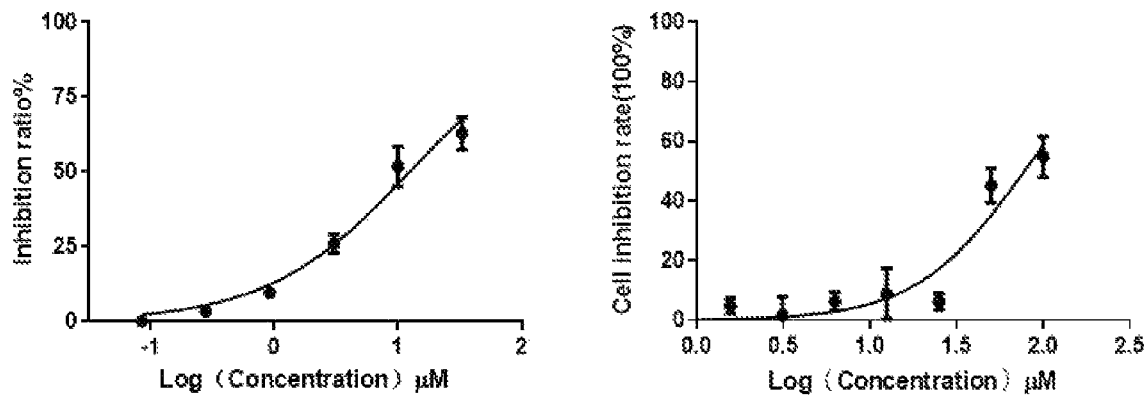
FIG. 6 illustrates an osteoclast differentiation inhibition curve and a RAW264.7-based cytotoxicity curve of Compound 6.
Figure 7:
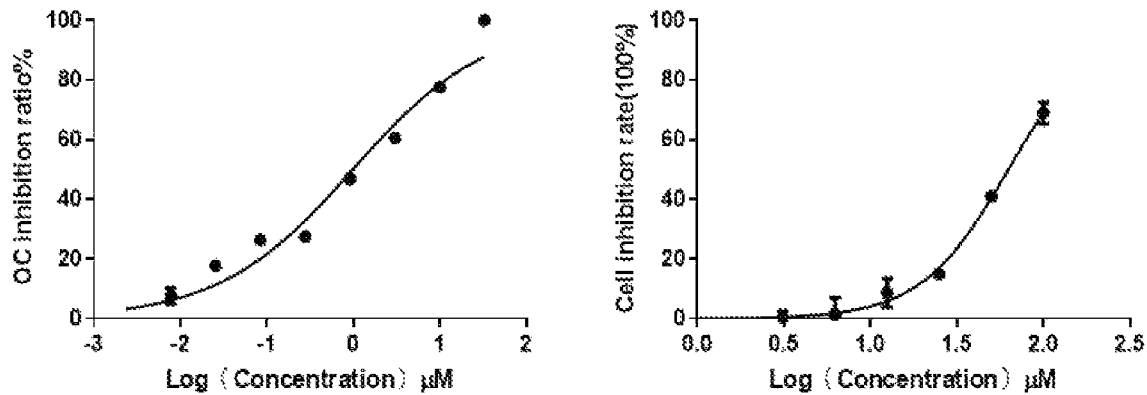
FIG. 7 illustrates an osteoclast differentiation inhibition curve and a RAW264.7-based cytotoxicity curve of Compound 7.
Figure 8:
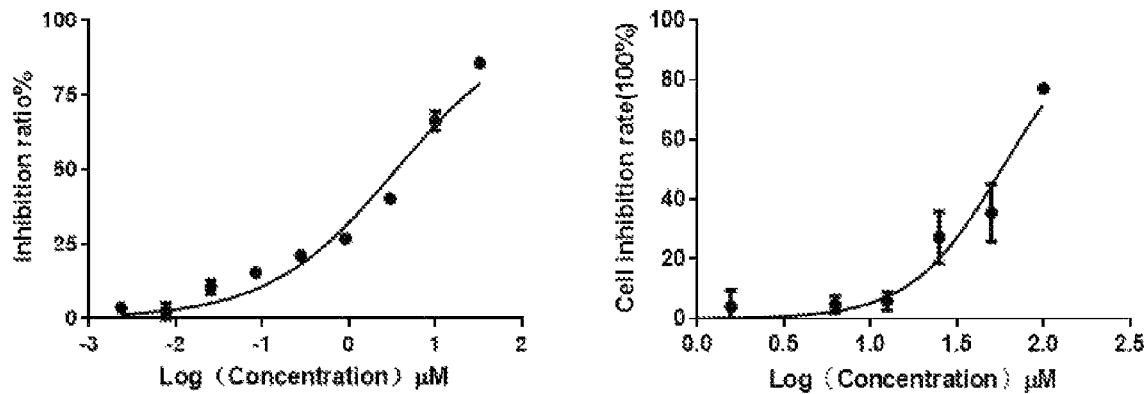
FIG. 8 illustrates an osteoclast differentiation inhibition curve and a RAW264.7-based cytotoxicity curve of Compound 8.
Figure 9:
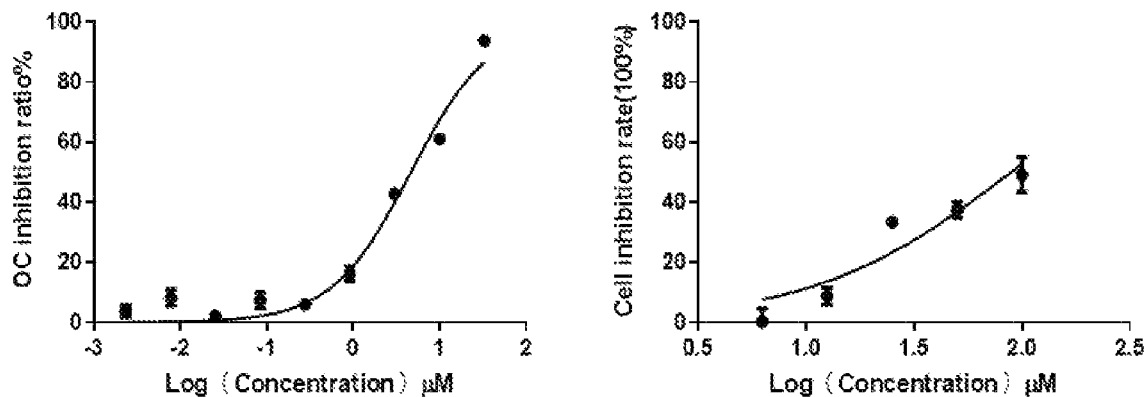
FIG. 9 illustrates an osteoclast differentiation inhibition curve and a RAW264.7-based cytotoxicity curve of Compound 9.
Figure 10:
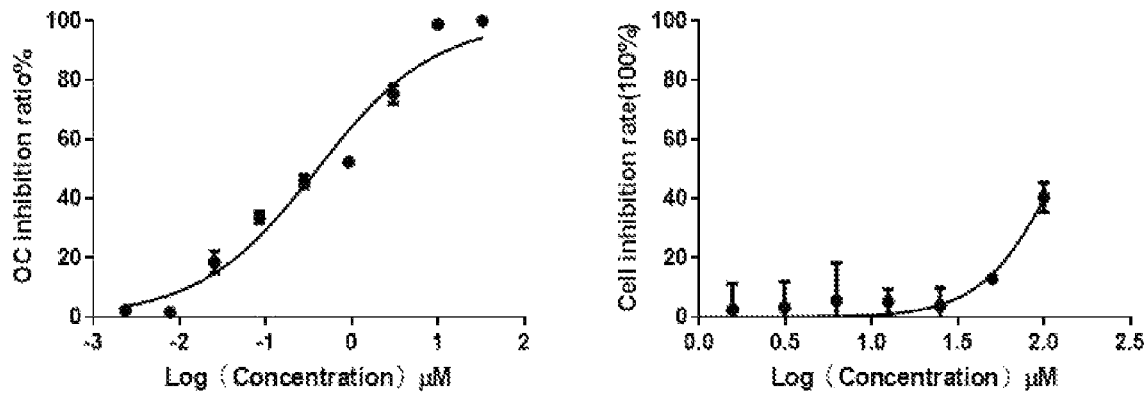
FIG. 10 illustrates an osteoclast differentiation inhibition curve and a RAW264.7-based cytotoxicity curve of Compound 10.
Figure 11:
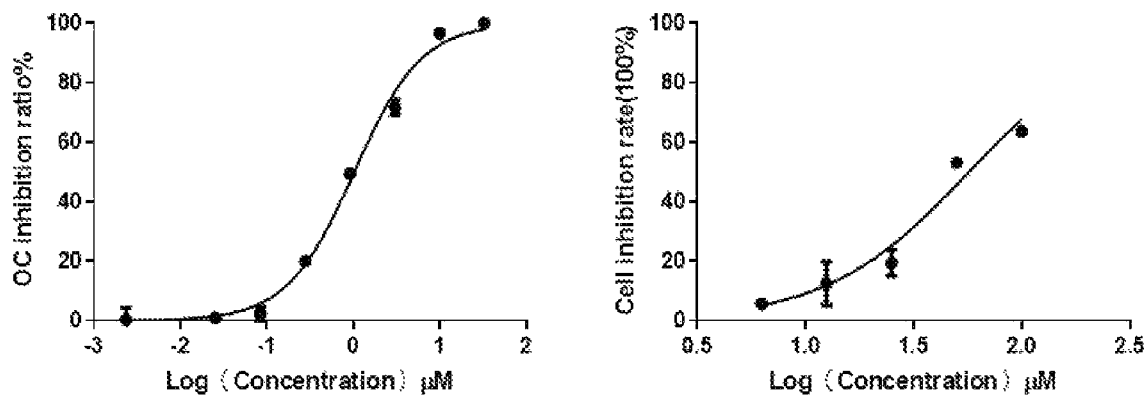
FIG. 11 illustrates an osteoclast differentiation inhibition curve and a RAW264.7-based cytotoxicity curve of Compound 11.
Figure 12:
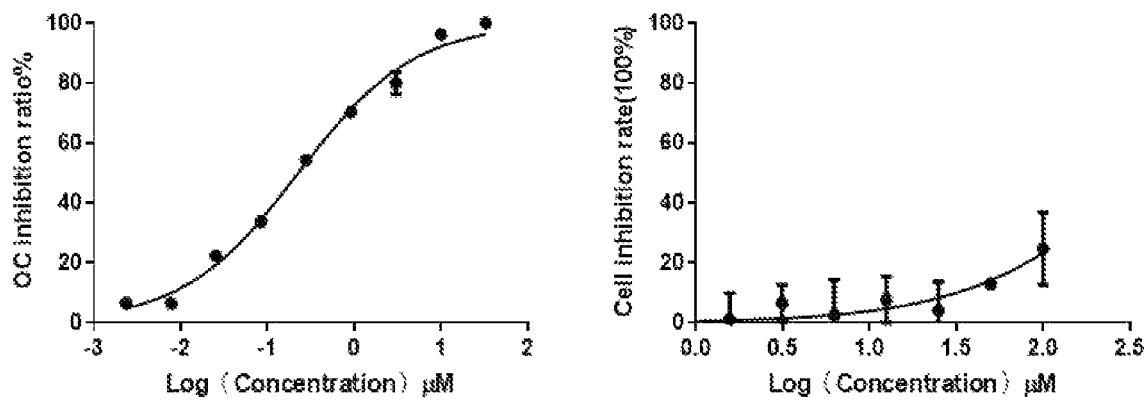
FIG. 12 illustrates an osteoclast differentiation inhibition curve and a RAW264.7-based cytotoxicity curve of Compound 12.
Figure 13:
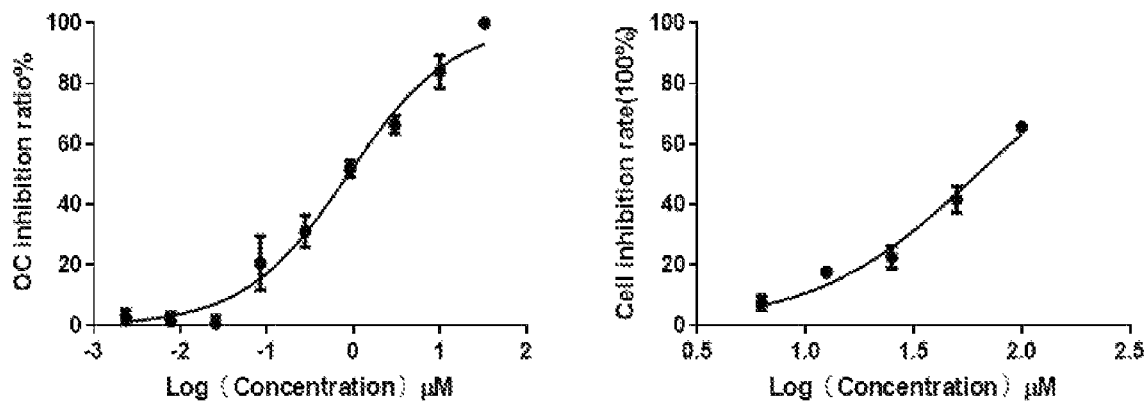
FIG. 13 illustrates an osteoclast differentiation inhibition curve and a RAW264.7-based cytotoxicity curve of Compound 13.
Figure 14:
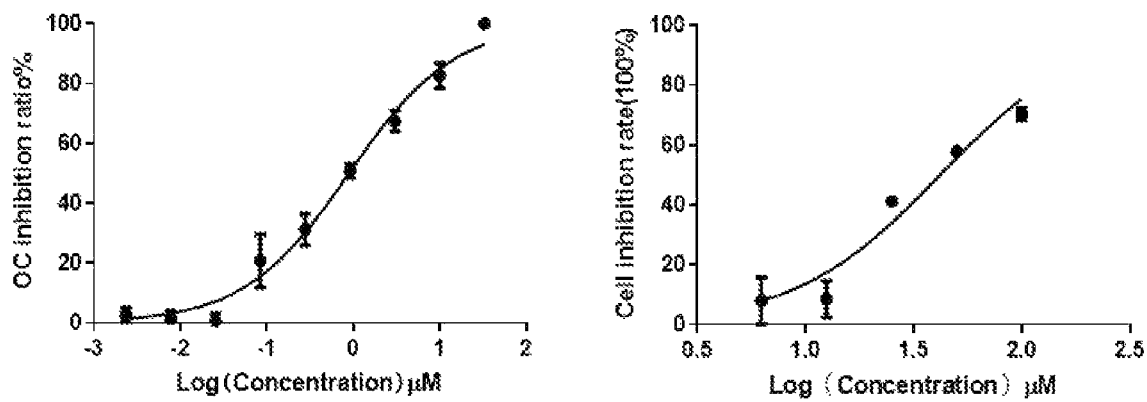
FIG. 14 illustrates an osteoclast differentiation inhibition curve and a RAW264.7-based cytotoxicity curve of Compound 14.
Figure 15:
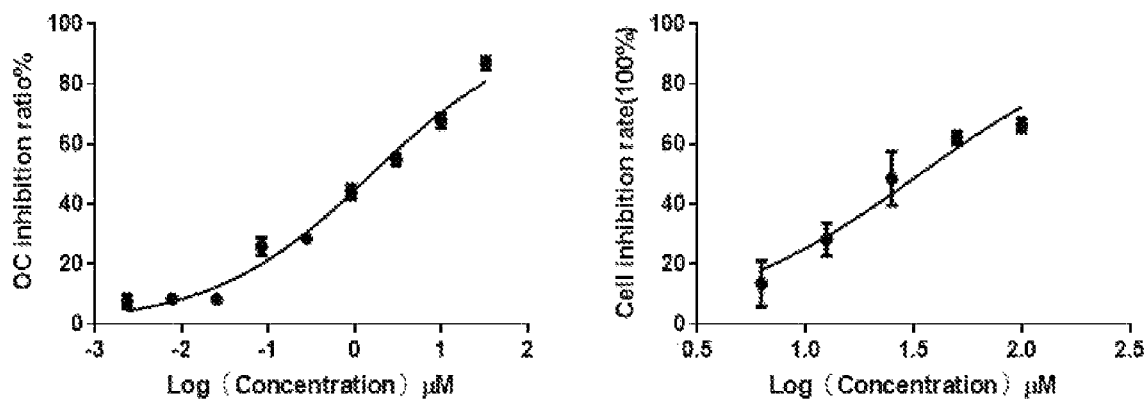
FIG. 15 illustrates an osteoclast differentiation inhibition curve and a RAW264.7-based cytotoxicity curve of Compound 15.
Figure 16:
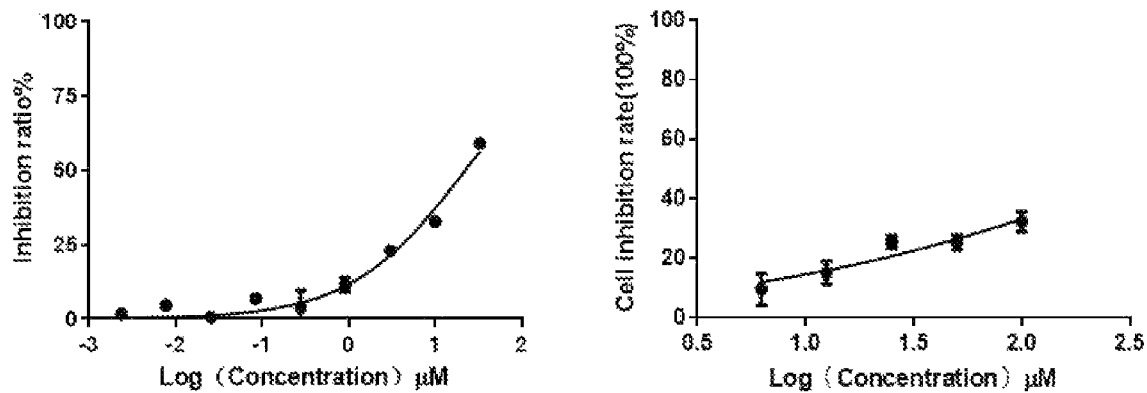
FIG. 16 illustrates an osteoclast differentiation inhibition curve and a RAW264.7-based cytotoxicity curve of Compound 16.
Figure 17:
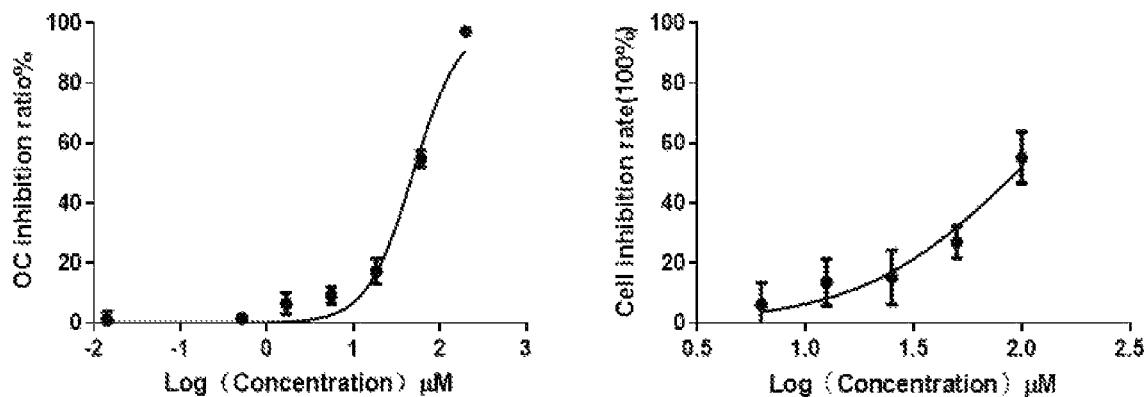
FIG. 17 illustrates an osteoclast differentiation inhibition curve and a RAW264.7-based cytotoxicity curve of Compound 17.
Figure 18:
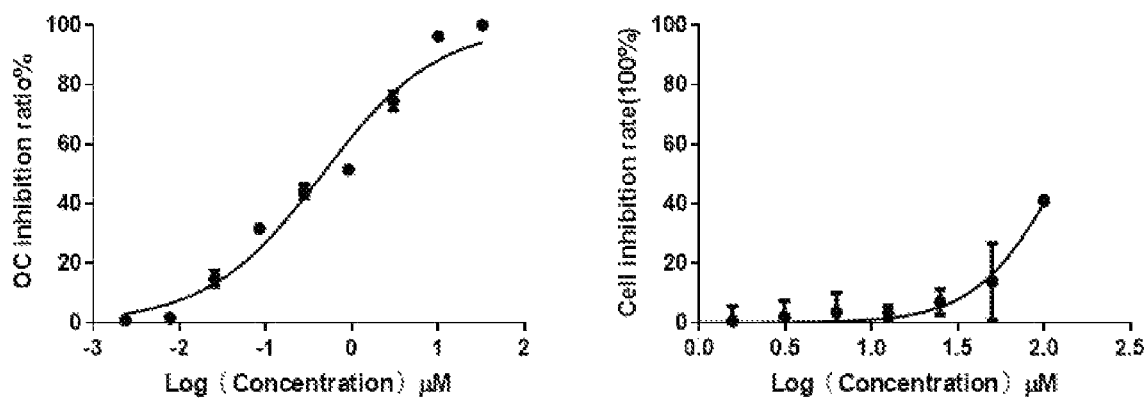
FIG. 18 illustrates an osteoclast differentiation inhibition curve and a RAW264.7-based cytotoxicity curve of Compound 18.
Figure 19:
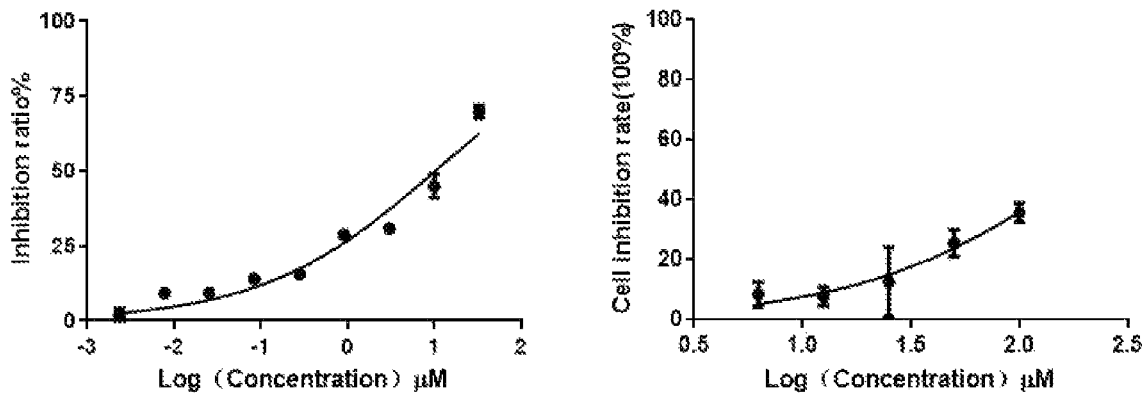
FIG. 19 illustrates an osteoclast differentiation inhibition curve and a RAW264.7-based cytotoxicity curve of Compound 19.
Figure 20:
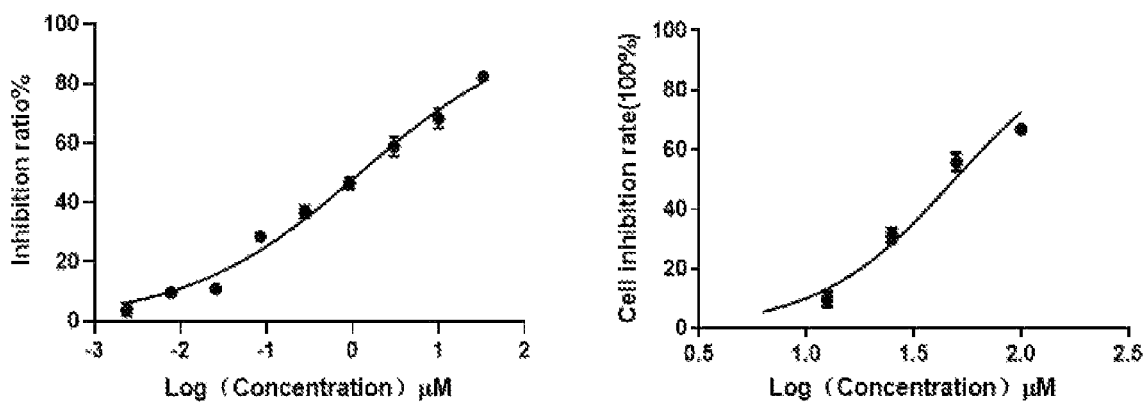
FIG. 20 illustrates an osteoclast differentiation inhibition curve and a RAW264.7-based cytotoxicity curve of Compound 20.
Figure 21:
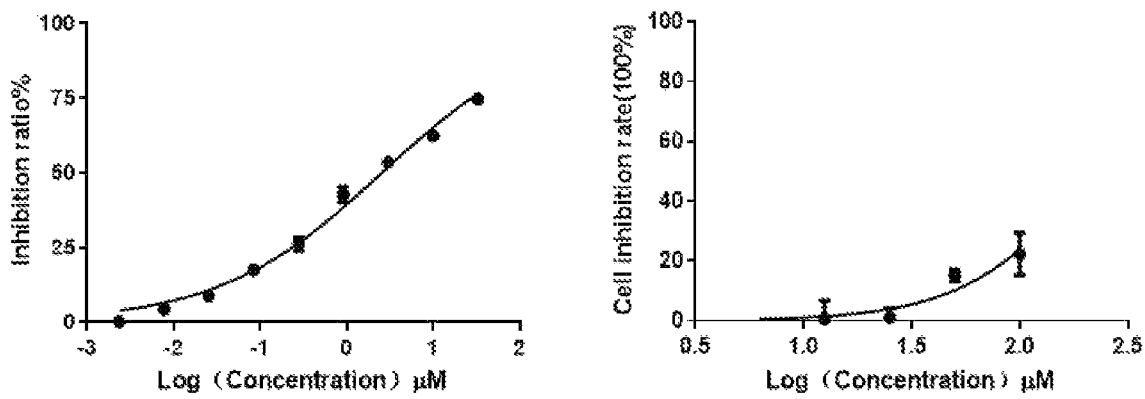
FIG. 21 illustrates an osteoclast differentiation inhibition curve and a RAW264.7-based cytotoxicity curve of Compound 21.
Figure 22:
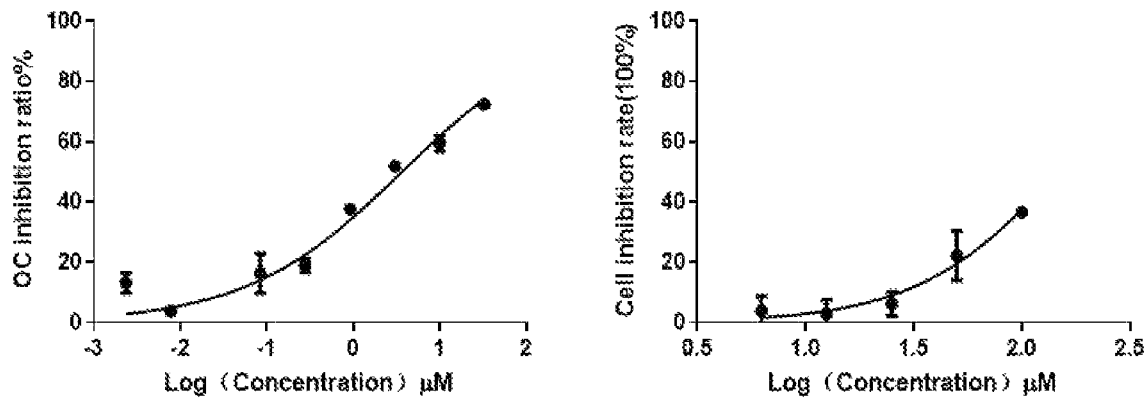
FIG. 22 illustrates an osteoclast differentiation inhibition curve and a RAW264.7-based cytotoxicity curve of Compound 22.
Figure 23:
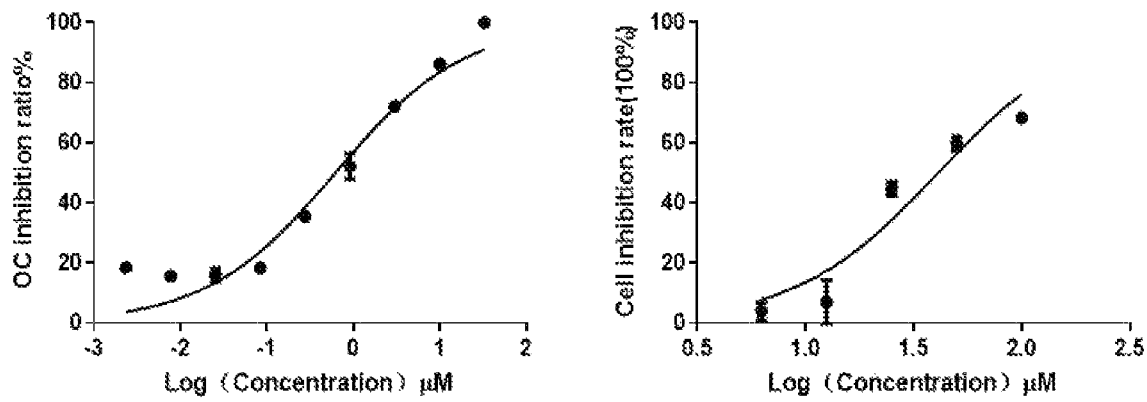
FIG. 23 illustrates an osteoclast differentiation inhibition curve and a RAW264.7-based cytotoxicity curve of Compound 23.
Figure 24:
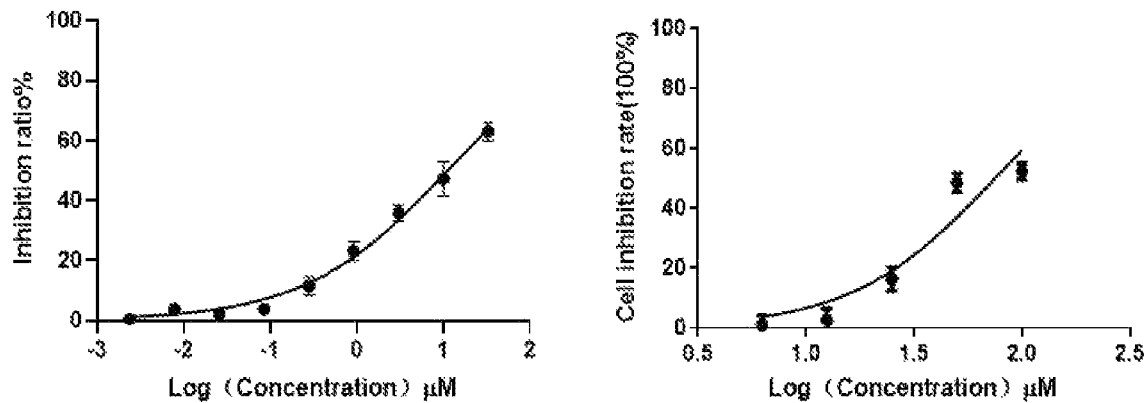
FIG. 24 illustrates an osteoclast differentiation inhibition curve and a RAW264.7-based cytotoxicity curve of Compound 24.
Figure 25:
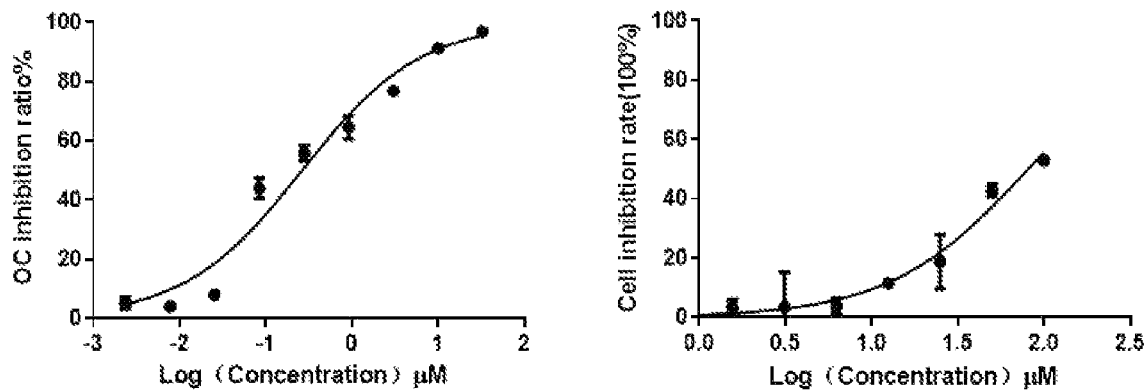
FIG. 25 illustrates an osteoclast differentiation inhibition curve and a RAW264.7-based cytotoxicity curve of Compound 25.
Figure 26:
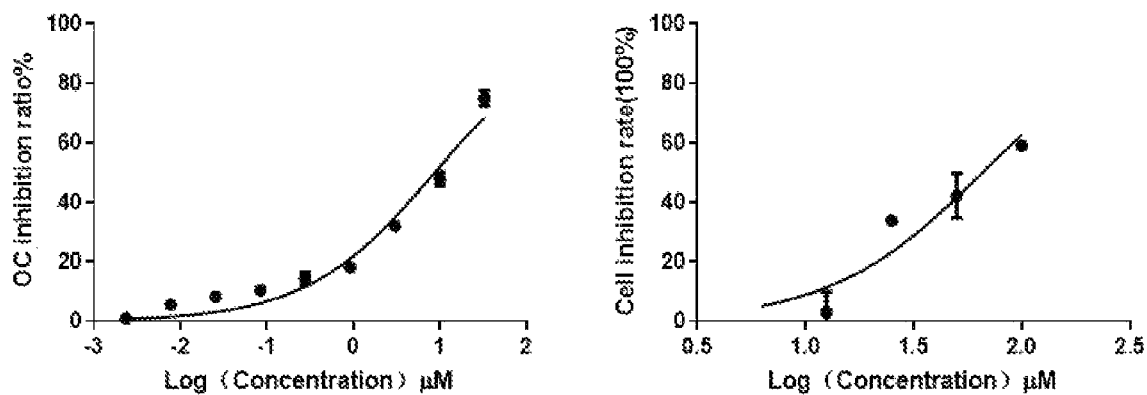
FIG. 26 illustrates an osteoclast differentiation inhibition curve and a RAW264.7-based cytotoxicity curve of Compound 26.
Figure 27:
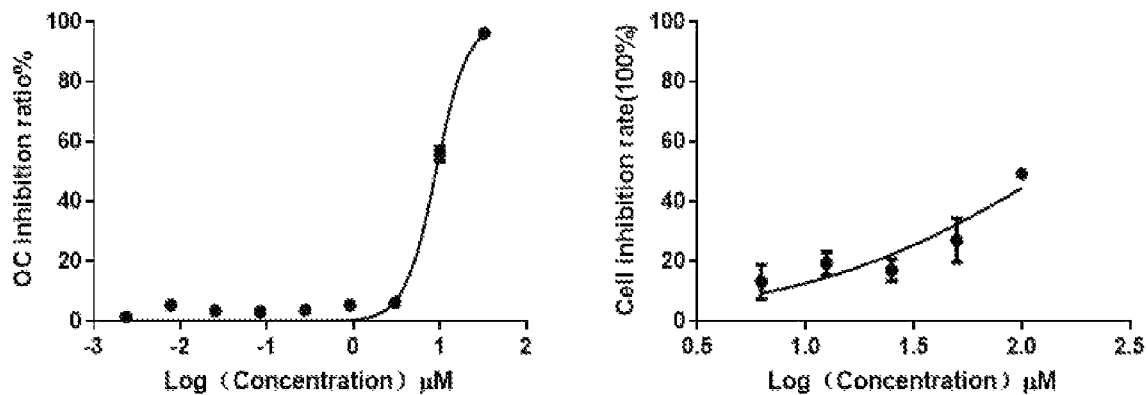
FIG. 27 illustrates an osteoclast differentiation inhibition curve and a RAW264.7-based cytotoxicity curve of Compound 27.
Figure 28:
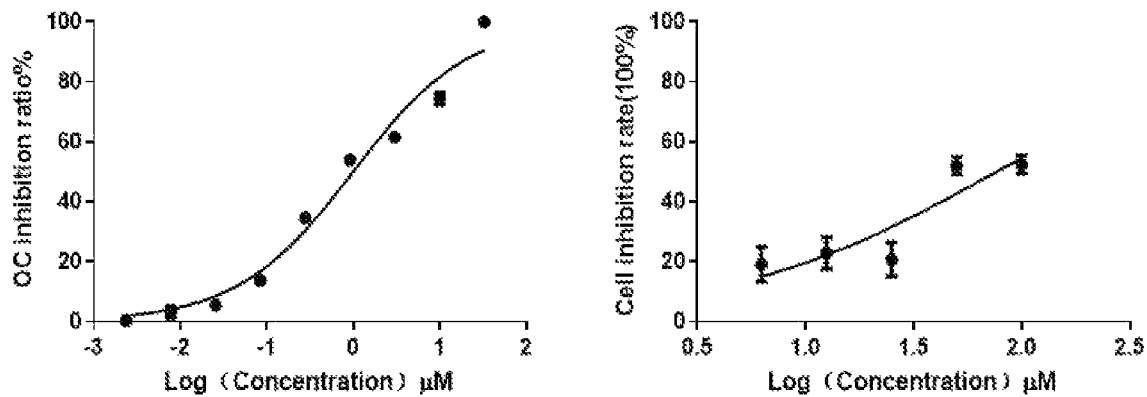
FIG. 28 illustrates an osteoclast differentiation inhibition curve and a RAW264.7-based cytotoxicity curve of Compound 28.
Figure 29:
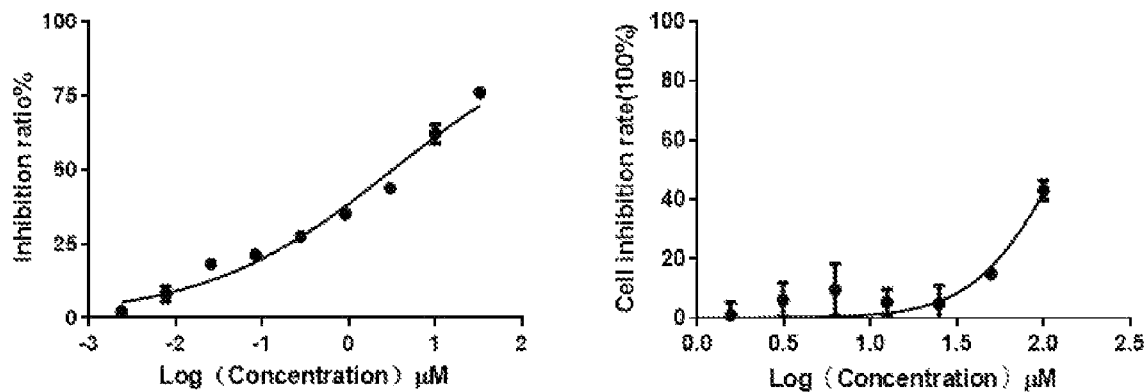
FIG. 29 illustrates an osteoclast differentiation inhibition curve and a RAW264.7-based cytotoxicity curve of Compound 29.
Figure 30:
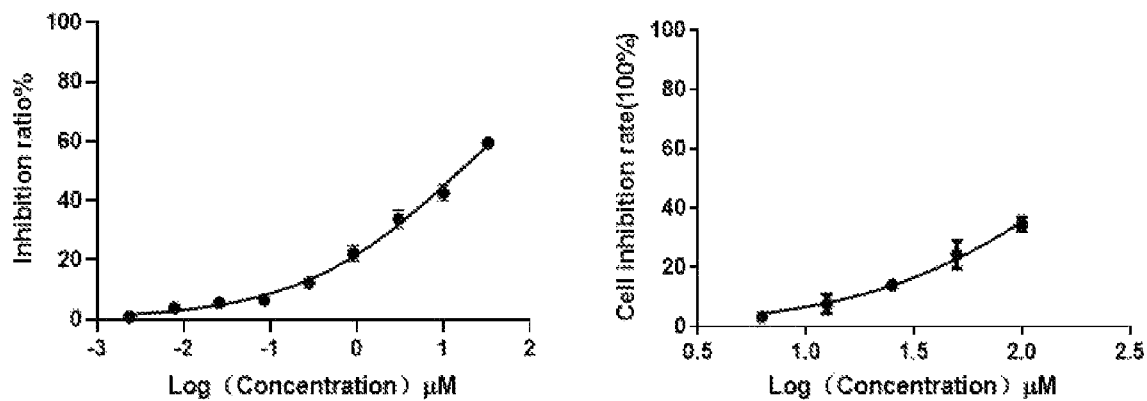
FIG. 30 illustrates an osteoclast differentiation inhibition curve and a RAW264.7-based cytotoxicity curve of Compound 30

The results in Table 1 reveal that, in the present disclosure, through the osteoclast differentiation inhibition experiment, five compounds were found to have different degrees of inhibitory effects on osteoclast differentiation. Among them, Compound 3 had the best activity and the highest therapeutic index, with $IC_{50}$ of 0.05 μM and SI of 1625 (see FIG. 1 and Table 1); Compound 12 took the second place of high activity with $IC_{50}$ of 0.23 μM and SI of 1701 (see FIG. 2 and Table 1); Compound 25 took the third place of high activity with $IC_{50}$ of 0.36 μM and SI of 301 (see FIG. 3 and Table 1); and Compound 10 and Compound 18 took the fourth and fifth places of high activity with $IC_{50}$ of 0.40 μM and SI of 308, and $IC_{50}$ of 0.46 μM and SI of 271, respectively (see FIG. 4, FIG. 5, and Table 1).

TABLE 1

Compounds obtained by screening and their inhibitory effects on osteoclast differentiation

| Compound No. | Cytotoxicity $CC_{50}$ (μM) | Osteoclast Inhibition $IC_{50}$ (μM) | Therapeutic index SI ($CC_{50}/IC_{50}$) |
|---|---|---|---|
| 1 | 62.50 | 1.24 | 50 |
| 2 | 69.21 | 0.73 | 95 |
| 3 | 81.24 | 0.05 | 1625 |
| 4 | 82.10 | 1.26 | 65 |
| 5 | 52.58 | 2.45 | 21 |
| 6 | 77.86 | 12.1 | 6 |
| 7 | 62.75 | 0.99 | 63 |
| 8 | 57.25 | 3.85 | 15 |
| 9 | 88.96 | 4.63 | 19 |
| 10 | 123.3 | 0.40 | 308 |
| 11 | 57.17 | 1.02 | 56 |
| 12 | 391.2 | 0.23 | 1701 |
| 13 | 62.31 | 0.88 | 71 |
| 14 | 41.94 | 0.89 | 47 |
| 15 | 33.85 | 1.56 | 22 |
| 16 | 450.9 | 22.30 | 20 |
| 17 | 93.93 | 49.61 | 2 |
| 18 | 124.8 | 0.46 | 271 |
| 19 | 201.9 | 10.2 | 20 |
| 20 | 49.10 | 1.23 | 40 |
| 21 | 220.5 | 2.58 | 85 |
| 22 | 148.9 | 3.66 | 41 |
| 23 | 41.15 | 0.78 | 53 |
| 24 | 75.18 | 11.11 | 7 |
| 25 | 81.24 | 0.27 | 301 |
| 26 | 65.76 | 8.85 | 7 |
| 27 | 135.3 | 9.03 | 15 |
| 28 | 76.25 | 0.99 | 77 |
| 29 | 119.2 | 3.21 | 37 |
| 30 | 197.8 | 15.36 | 13 |

The present disclosure finds a series of thiazolamide derivatives through computer-aided drug design similarity retrieval. Through the osteoclast differentiation inhibition experiment and the cytotoxicity assay (MTT), it was found that among these compounds, each of Compounds 3, 10, 12, 18 and 25 had osteoclast differentiation inhibition activity of less than 0.5 μM, low cytotoxicity, and high therapeutic index. Compound 3 has a half inhibitory dose for osteoclast differentiation inhibition ($IC_{50}$) of 0.05 μM, a median lethal dose of cells ($CC_{50}$) of 81.24 μM, and a selective inhibition constant (SI) of 1625 (see FIG. 1 and Table 1); Compound 12 has a median effective dose for osteoclast differentiation inhibition ($IC_{50}$) of 0.23 μM, a median lethal dose of cells ($CC_{50}$) of 391.2 μM, and a selective inhibition constant (SI) of 1701 (see FIG. 2 and Table 1); Compound 25 has a half inhibitory dose for osteoclast differentiation inhibition ($IC_{50}$) of 0.27 μM, a median lethal dose of cells ($CC_{50}$) of 81.24 μM, and a selective inhibition constant (SI) of 301 (see FIG. 3 and Table 1); Compound 10 has a half inhibitory dose for osteoclast differentiation inhibition ($IC_{50}$) of 0.40 μM, a median lethal dose of cells ($CC_{50}$) of 123.3 μM, and a selective inhibition constant (SI) of 308 (see FIG. 4 and Table 1); and Compound 18 has a half inhibitory dose for osteoclast differentiation inhibition ($IC_{50}$) of 0.46 μM, a median lethal dose of cells ($CC_{50}$) of 124.8 μM, and a selective inhibition constant (SI) of 271 (see FIG. 5 and Table 1). The results indicate that these compounds have high inhibitory activity on osteoclast differentiation and low cytotoxicity, and can be used as a class of osteoclast inhibitors for preparing medicaments for prevention and treatment of osteoporosis or osteopenia.

In the description of this specification, the description referring to the terms "an embodiment", "some embodiments", "an example", "specific examples", or "some examples" means that the specific features, structures, materials or characteristics described in conjunction with the embodiment or example are included in at least one embodiment or example of the present disclosure. In this specification, the schematic expression of the above terms does not necessarily refer to the same embodiment or example. Moreover, the described specific features, structures, mate-

What is claimed is:

1. A method for treating or preventing osteoporosis or osteopenia, the method comprising: administering a compound having one of the following structures or a stereoisomer, geometric isomer, tautomer, nitrogen oxide, hydrate, or solvate thereof, or a pharmaceutically acceptable salt or prodrug of the compound having one of the following structures to a patient:

1

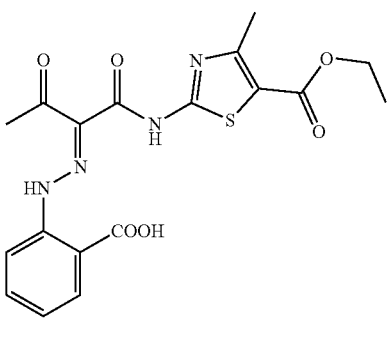

2

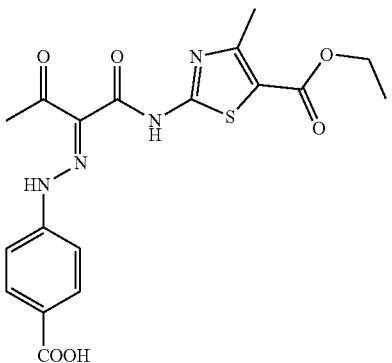

3

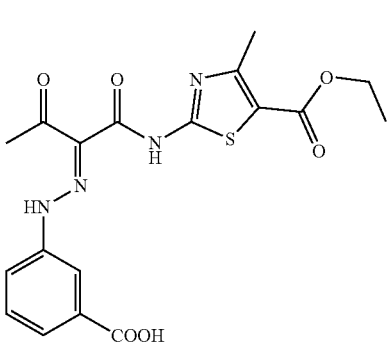

-continued

4

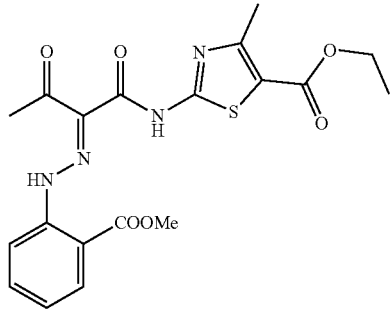

5

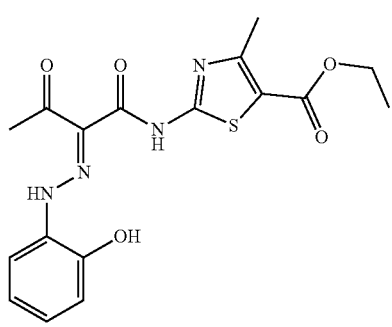

6

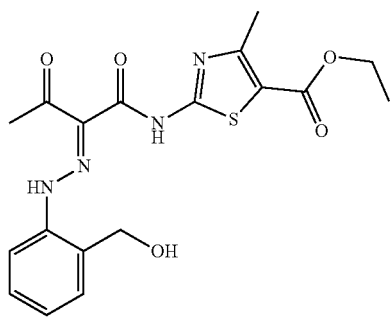

7

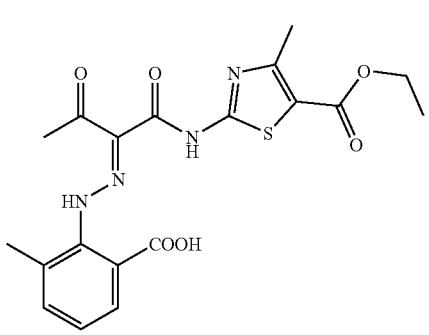

8

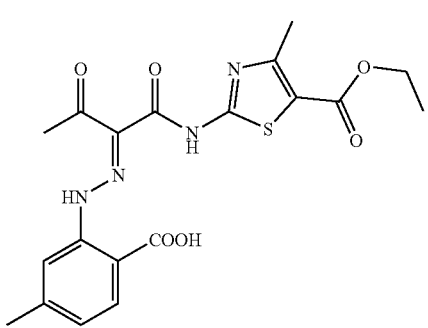

9
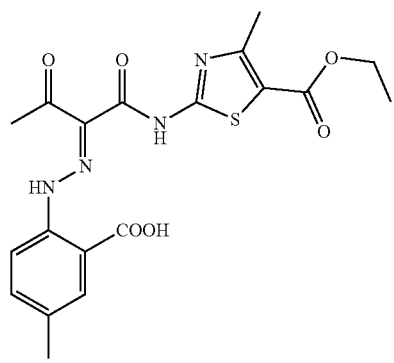
10
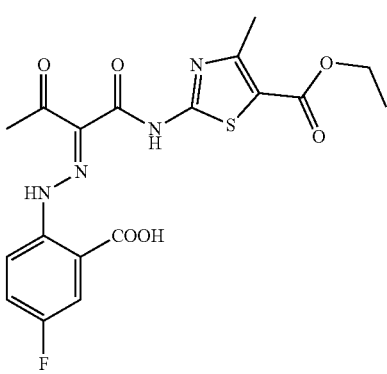
11
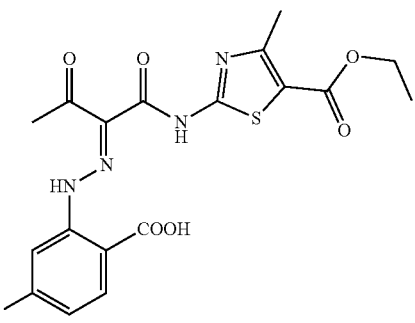
12
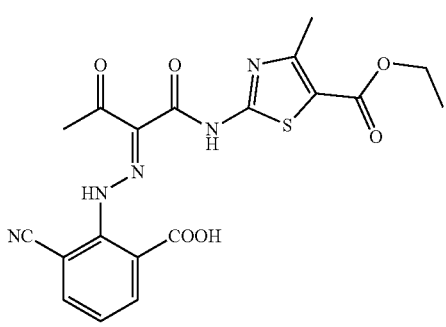
13
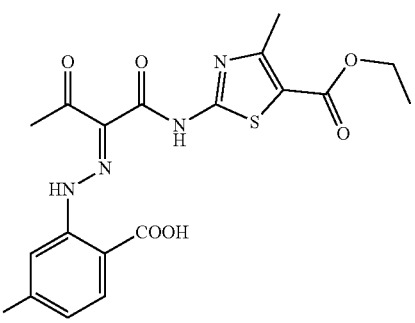
14
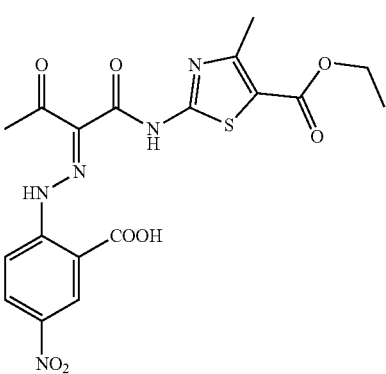
15
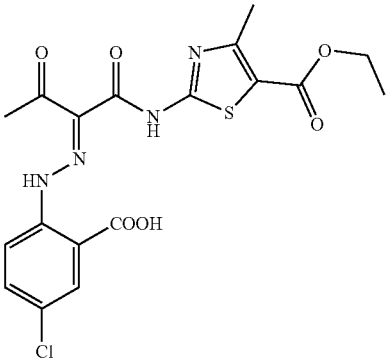
16
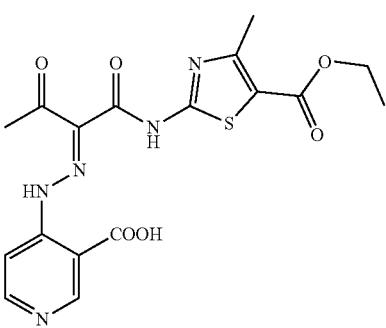

-continued
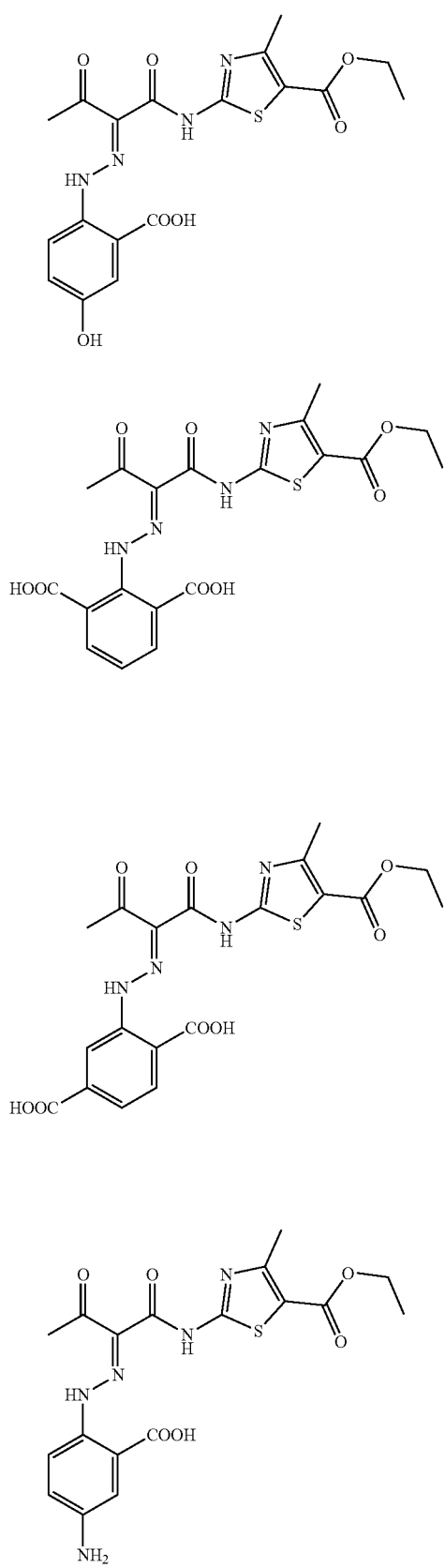
17
18
19
20
-continued
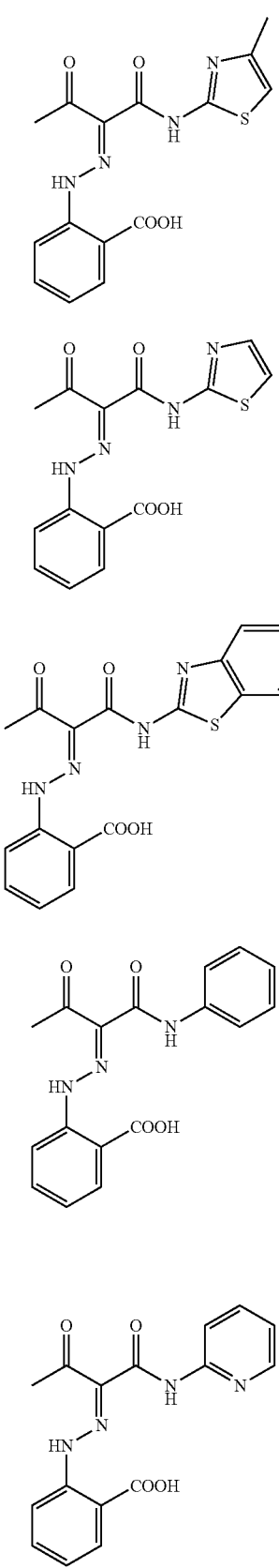
21
22
23
24
25

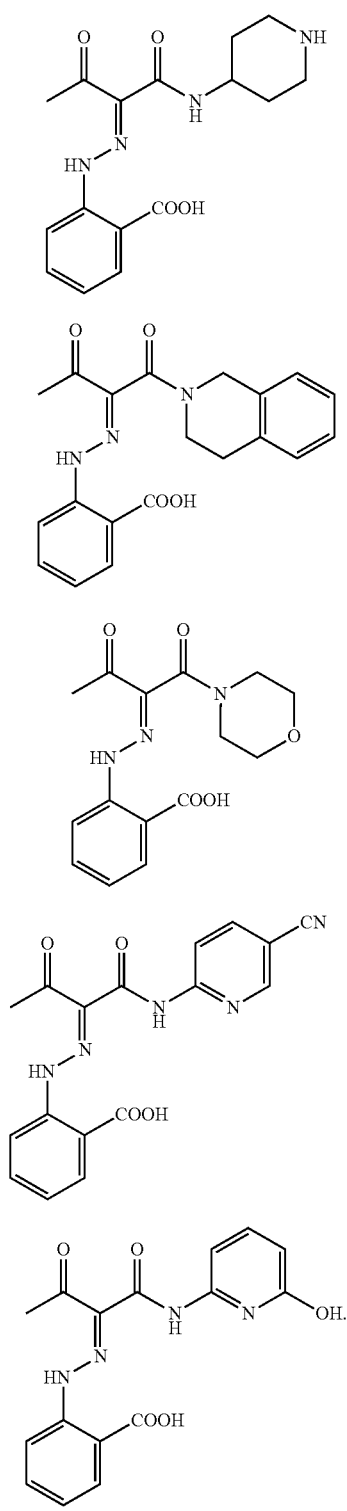

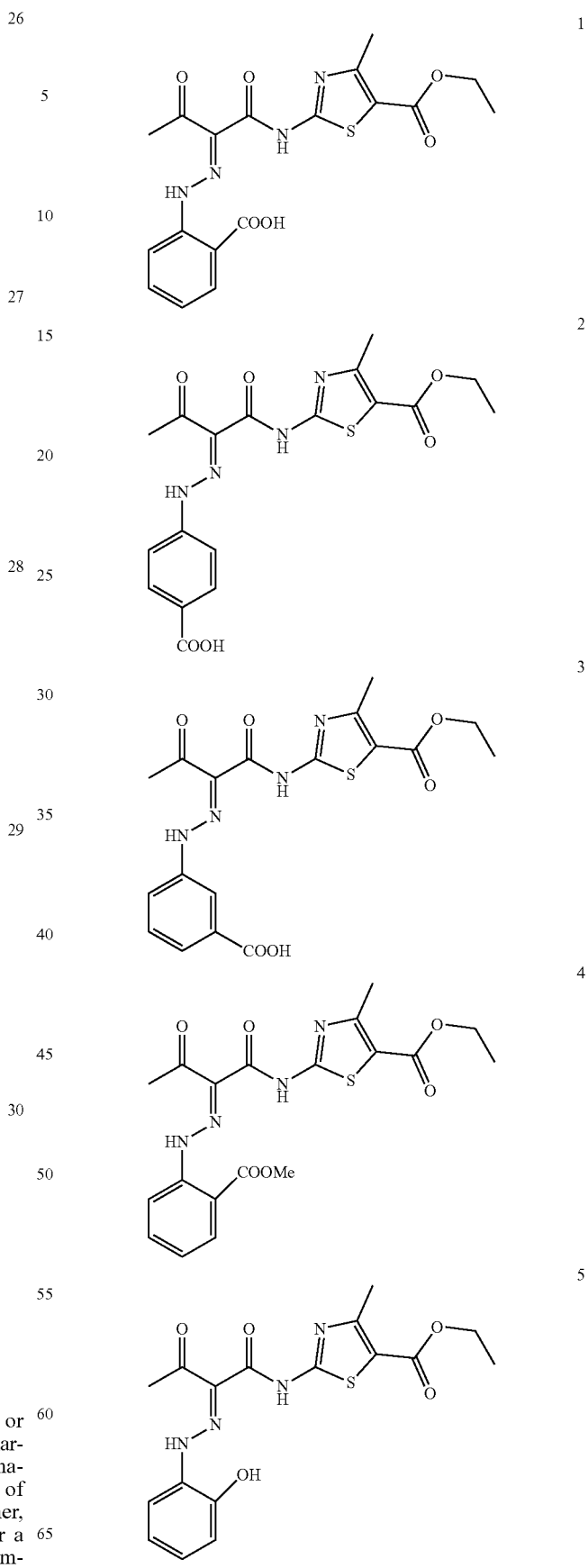

2. A method for treating or preventing osteoporosis or osteopenia, the method comprising: administering a pharmaceutical composition to a patient, wherein the pharmaceutical composition comprises a compound having one of the following structures or a stereoisomer, geometric isomer, tautomer, nitrogen oxide, hydrate, or solvate thereof, or a pharmaceutically acceptable salt or prodrug of the compound having one of the following structures:

6
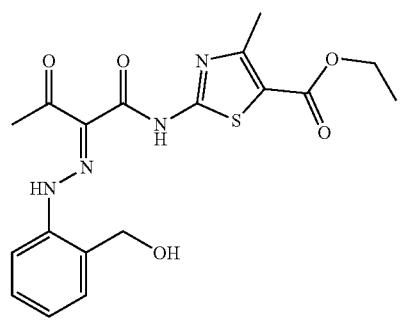
7
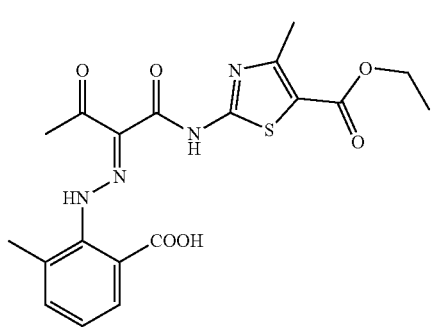
8
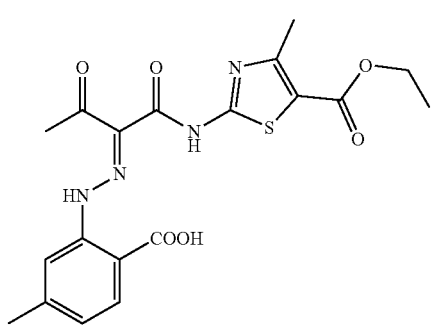
9
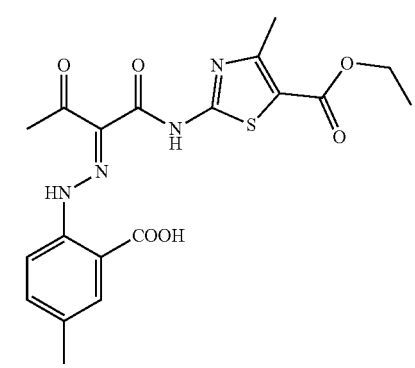
10
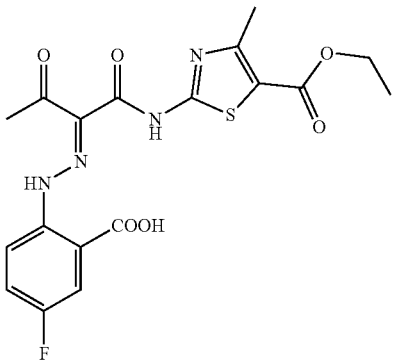
11
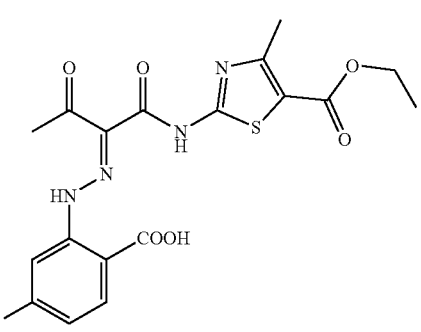
12
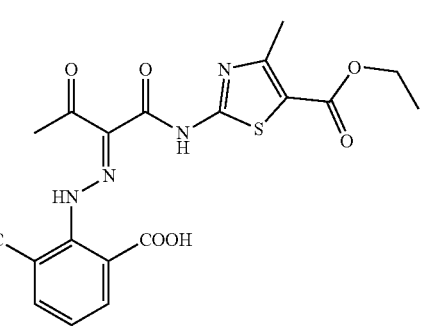
13
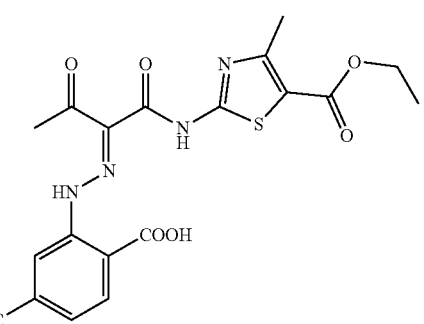

14
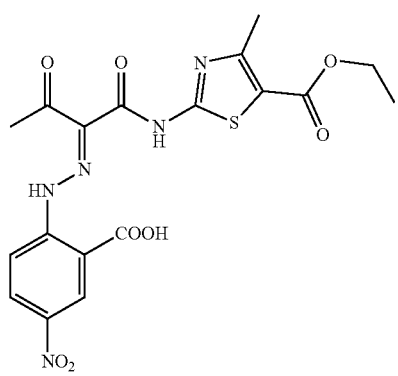
15
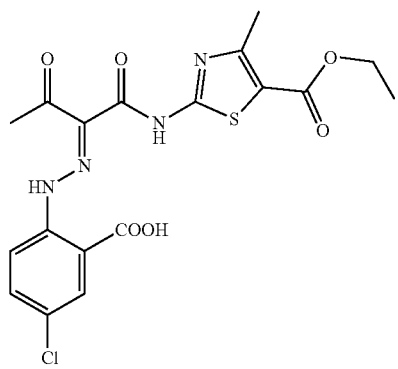
16
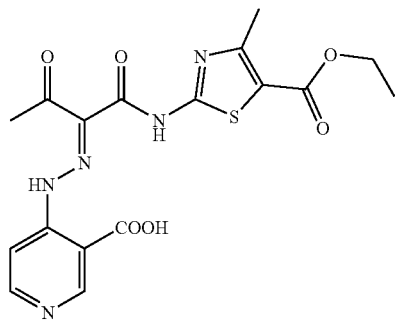
17
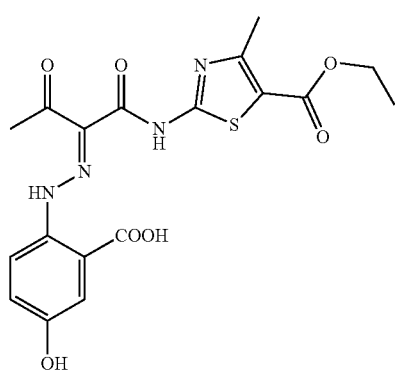
18
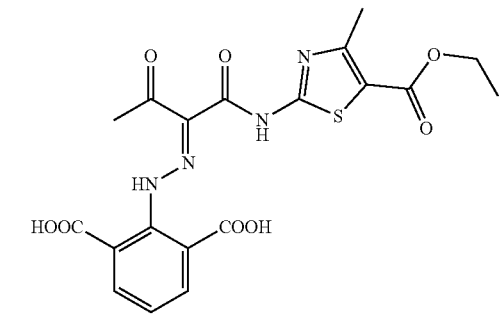
19
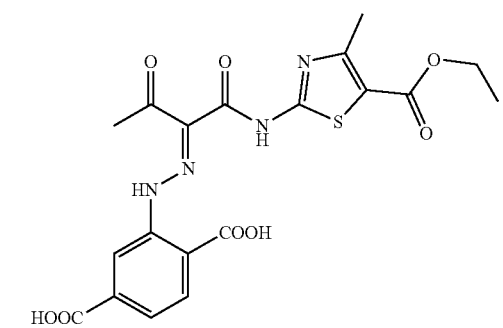
20
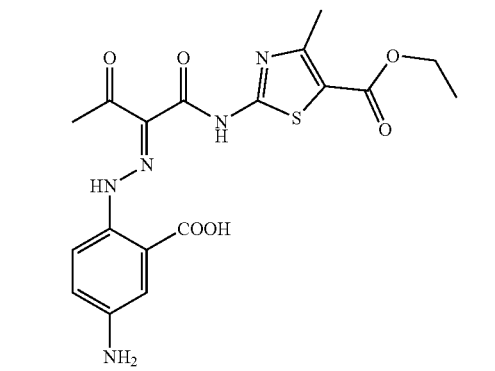
21
22
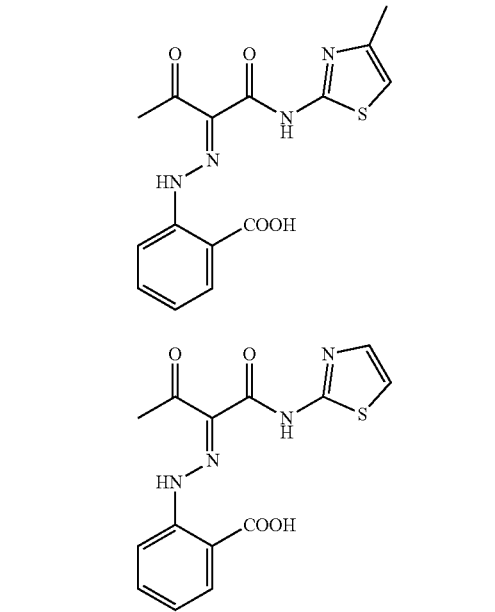

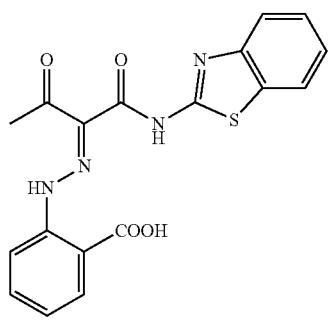
23
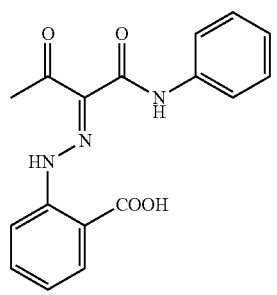
24
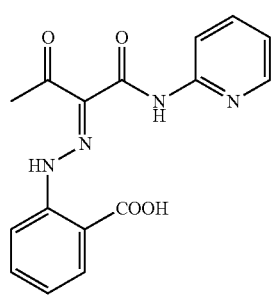
25
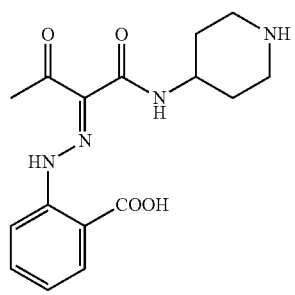
26
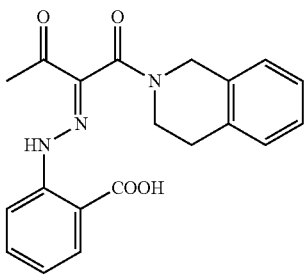
27
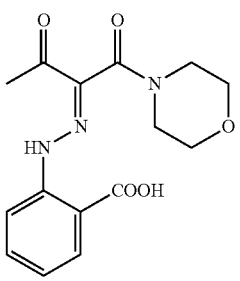
28
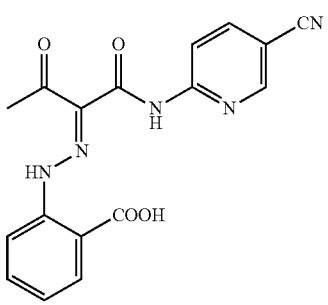
29
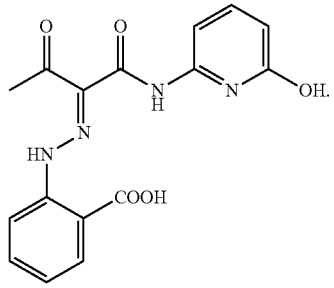
30
or
* * * * *